(12) United States Patent
Fodor et al.

(10) Patent No.: US 6,284,460 B1
(45) Date of Patent: Sep. 4, 2001

(54) HYBRIDIZATION AND SEQUENCING OF NUCLEIC ACIDS USING BASE PAIR MISMATCHES

(75) Inventors: Stephen P. A. Fodor; Robert J. Lipshutz, both of Palo Alto; Xiaohua Huang, Mt. View, all of CA (US)

(73) Assignee: Affymetrix Inc., Santa Clara, CA (US)

( * ) Notice: Subject to any disclaimer, the term of this patent is extended or adjusted under 35 U.S.C. 154(b) by 0 days.

(21) Appl. No.: 08/877,196

(22) Filed: Jun. 17, 1997

Related U.S. Application Data

(63) Continuation of application No. 08/505,919, filed on Jul. 24, 1995, now abandoned, which is a continuation of application No. 08/082,937, filed on Jun. 25, 1993, now abandoned.

(51) Int. Cl.⁷ .................................................. C12Q 1/68
(52) U.S. Cl. .......................... 435/6; 536/24.3; 536/24.33; 536/24.31
(58) Field of Search ............................. 435/6; 536/24.3, 536/24.33, 24.31

(56) References Cited

U.S. PATENT DOCUMENTS

| | | | |
|---|---|---|---|
| 5,002,867 | 3/1991 | Macevicz | 435/6 |
| 5,143,854 | 9/1992 | Pirrung et al. | 436/518 |
| 5,202,231 | 4/1993 | Drmanac et al. | 435/6 |
| 5,273,632 | * 12/1993 | Stockham et al. | 204/180.1 |
| 5,492,806 | 2/1996 | Drmanac et al. | 435/5 |
| 5,525,464 | 6/1996 | Drrmanac et al. | 435/6 |
| 5,527,681 | 6/1996 | Holmes | 435/6 |

FOREIGN PATENT DOCUMENTS

| | | | |
|---|---|---|---|
| 0392546 | 10/1990 | (EP) | C12Q/1/68 |
| WO 89/11548 | 11/1989 | (WO) | C12Q/1/68 |
| WO 90/00626 | 1/1990 | (WO) | C12Q/1/68 |
| WO 90/03382 | 4/1990 | (WO) | C07H/21/00 |
| WO 92/10092 | 6/1992 | (WO) | A01N/1/02 |
| WO 92/10588 | 6/1992 | (WO) | C12Q/1/68 |
| WO 93/17126 | 9/1993 | (WO) | C12Q/1/68 |

OTHER PUBLICATIONS

Chetverin, A.B. and Kramer, F.R., "Novel Oligonucleotide Arrays and Their Use for Sorting, Isolating, Sequencing and Manipulating Nucleic Acids," pp. 1–67 and attached Figures (publication journal title and date unknown).

Chetverin, A.B. and Kramer, F.R., "Sequencing of Pools of Nucleic Acids on Oligonucleotide Arrays," *BioSystems*, (1993) 30:215–231.

(List continued on next page.)

*Primary Examiner*—Scott W. Houtteman
(74) *Attorney, Agent, or Firm*—Pillsbury Madison Sutro LLP

(57) ABSTRACT

Devices and techniques for hybridization of nucleic acids and for determining the sequence of nucleic acids. Arrays of nucleic acids are formed by techniques, preferably high resolution, light-directed techniques. Positions of hybridization of a target nucleic acid are determined by, e.g., epifluorescence microscopy. Devices and techniques are proposed to determine the sequence of a target nucleic acid more efficiently and more quickly through such synthesis and detection techniques.

16 Claims, 17 Drawing Sheets

OTHER PUBLICATIONS

Chetverin, A.B. and Kramer, F.R., "Total Genome Sequencing With Oligonucleotide Arrays," pp. 1–26 (publication journal title and date unknown).

Elder, "Analysis of DNA Oligonucleotide Hybridization Data by Maximum Entropy," *Maximum Entropy and Bayesian Methods* Paris, 1992, pp. 1–10.

Hagstrom et al., "Maximum Likelihood Genetic Sequence Reconstruction from Oligo Content," Sep. 1992, Argonne Nat'l Laboratory Preprint MCS–P309–0592.

Lipshutz, "Likelihood DNA Sequencing By Hybridization," *J. Biomolecular Structure & Dynamics* (1993) 11:637–653.

Southern et al., "Analyzing and Comparing Nucleic Acid Sequences by Hybridization to Arrays of Oligonucleotides: Evaluation Using Experimental Models," *Genomics* (1992) 13:1008–1017.

Sanger et al., "DNA sequencing with chain–terminating inhibitors," *Proc. Natl. Acad. Sci. USA* (1977) 74:5463–5467.

Maxam et al., "A new method for sequencing DNA," *Proc. Natl. Acad. Sci. USA* (1977) 74:560–564.

Khrapko, et al., An oligonucleotide hybridization approach to DNA sequencing, *FEBS Letters*, 256:118–122 (1989).

Lysov et al., "A New Method for Determining the DNA Nucleotide Sequence by Hybridization with Oligonucleotides," (Translation) *Doklady Akademii Nauk SSSR*, 303(6):1508–1511 (1988).

Abstract, Sequencing of Megabase Plus DNA by Hybridization: Theory of the Method, Drmanac et al. Apr., 1988.

Poster, Cold Spring Harbor Symposium on Genome Mapping and Sequencing, Apr., 1988.

Thesis, "Subfragments as Informative Characteristics of DNA Molecules—Computer Simulation" by Ivan Labat, Apr. 6, 1988.

Wallace et al, Nucleic Acids Res., 6:3545–3557 (1979).

Church et al, Proc. Natl. Acad. Sci. USA, 81:1991–1995, Apr., 1984.

Sambrook et al., Molecular Cloning, p. 11.45–11.47, 1989.*

Stratagene 1988 Catalog p. 39.*

* cited by examiner

A P$_3$ P$_4$ P$_5$
T P$_3$ P$_4$ P$_5$
C P$_3$ P$_4$ P$_5$
T P$_3$ P$_4$ P$_5$
*FIG. 12c*
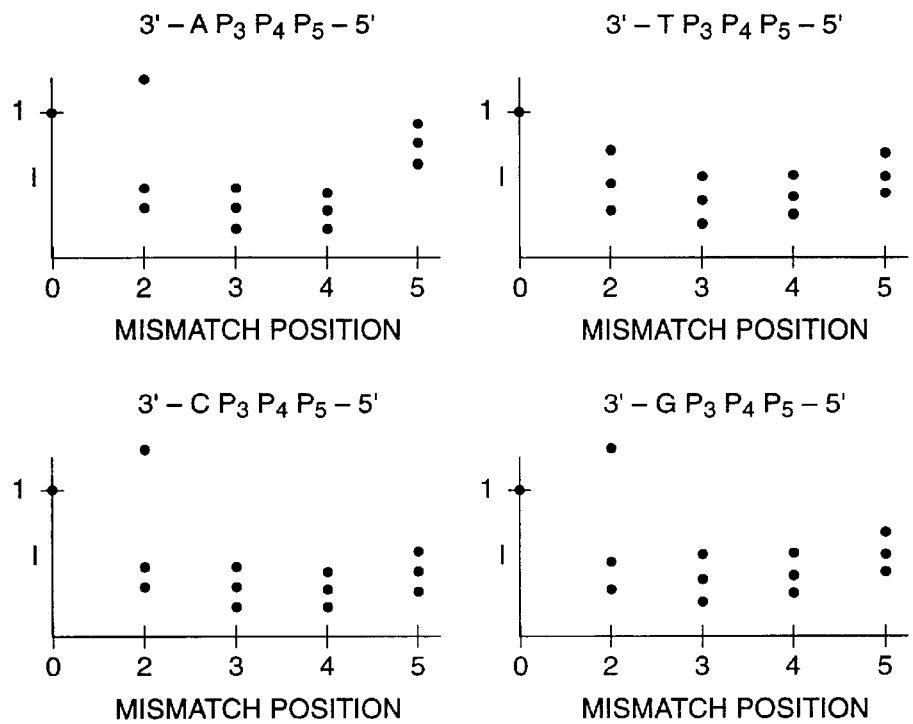
*FIG. 12d*
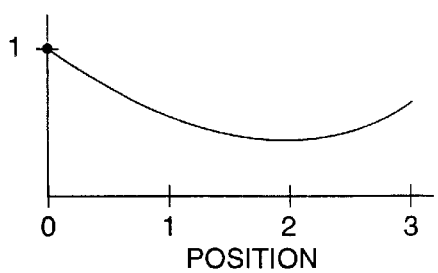
*FIG. 15a*
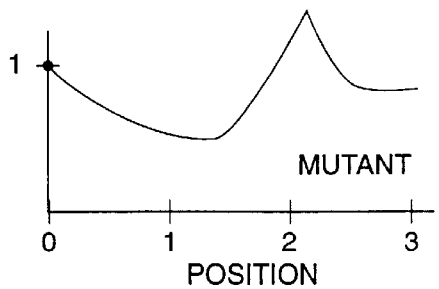
*FIG. 15b*

HYBRIDIZATION AND SEQUENCING OF NUCLEIC ACIDS USING BASE PAIR MISMATCHES

This is a Continuation of application Ser. No. 08/505,919 Jul. 24, 1995, abandoned, which is a continuation of application Ser. No. 08/082,937, filed Jun. 25, 1993, now abandoned.

GOVERNMENT RIGHTS

The invention described herein arose in the course of or under Contract No. DE-FG03-92ER81275 (Grant No. 21012-92-II) between the Department of Energy and Affymax; and in the course of or under NIH Contract No. 1R01HG00813-01.

BACKGROUND OF THE INVENTION

The present invention relates to the field of nucleic acid analysis, detection, and sequencing. More specifically, in one embodiment the invention provides improved techniques for synthesizing arrays of nucleic acids, hybridizing nucleic acids, detecting mismatches in a double-stranded nucleic acid composed of a single-stranded probe and a target nucleic acid, and determining the sequence of DNA or RNA or other polymers.

It is important in many fields to determine the sequence of nucleic acids because, for example, nucleic acids encode the enzymes, structural proteins, and other effectors of biological functions. In addition to segments of nucleic acids that encode polypeptides, there are many nucleic acid sequences involved in control and regulation of gene expression.

The human genome project is one example of a project using nucleic acid sequencing techniques. This project is directed toward determining the complete sequence of the genome of the human organism. Although such a sequence would not necessarily correspond to the sequence of any specific individual, it will provide significant information as to the general organization and specific sequences contained within genomic segments from particular individuals. The human genome project will also provide mapping information useful for further detailed studies.

The need for highly rapid, accurate, and inexpensive sequencing technology is nowhere more apparent than in a demanding sequencing project such as the human genome project. To complete the sequencing of a human genome will require the determination of approximately $3 \times 10^9$, or 3 billion, base pairs.

The procedures typically used today for sequencing include the methods described in Sanger et al., *Proc. Natl. Acad. Sci. USA* (1977) 74:5463–5467, and Maxam et al., *Methods in Enzymology* (1980) 65:499–559. The Sanger method utilizes enzymatic elongation with chain terminating dideoxy nucleotides. The Maxam and Gilbert method uses chemical reactions exhibiting base-specific cleavage reactions. Both methods require a large number of complex manipulations, such as isolation of homogeneous DNA fragments, elaborate and tedious preparation of samples, preparation of a separating gel, application of samples to the gel, electrophoresing the samples on the gel, working up of the finished gel, and analysis of the results of the procedure.

Alternative techniques have been proposed for sequencing a nucleic acid. PCT patent Publication No. 92/10588, incorporated herein by reference for all purposes, describes one improved technique in which the sequence of a labeled, target nucleic acid is determined by hybridization to an array of nucleic acid probes on a substrate. Each probe is located at a positionally distinguishable location on the substrate. When the labeled target is exposed to the substrate, it binds at locations that contain complementary nucleotide sequences. Through knowledge of the sequence of the probes at the binding locations, one can determine the nucleotide sequence of the target nucleic acid. The technique is particularly efficient when very large arrays of nuleic acid probes are utilized. Such arrays can be formed according to the techniques described in U.S. Pat. No. 5,143,854 issued to Pirrung et al. See also U.S. application Ser. No. 07/805,727, both incorporated herein by reference for all purposes.

When the nucleic acid probes are of a length shorter than the target, one can employ a reconstruction technique to determine the sequence of the larger target based on affinity data from the shorter probes. See U.S. Pat. No. 5,202,231 to Drmanac et al., and PCT patent Publication No. 89/10977 to Southern. One technique for overcoming this difficulty has been termed sequencing by hybridization or SBH. For example, assume that a 12-mer target DNA 5'-AGCCTAGCTGAA (SEQ. ID NO:1) is mixed with an array of all octanucleotide probes. If the target binds only to those probes having an exactly complementary nucleotide sequence, only five of the 65,536 octamer probes (3'-TCGGATCG, CGGATCGA, GGATCGAC, GATCGACT, and ATCGACTT) will hybridize to the target. Alignment of the overlapping sequences from the hybridizing probes reconstructs the complement of the original 12-mer target:

```
TCGGATCG
 CGGATCGA
  GGATCGAC
   GATCGACT
    ATCGACTT
TCGGATCGACTT (SEQ. ID NO:2)
```

While meeting with much optimism, prior techniques have also met with certain limitations. For example, practitioners have encountered substantial difficulty in analyzing probe arrays hybridized to a target nucleic acid due to the hybridization of partially mismatched sequences, among other difficulties. The present invention provides significant advances in sequencing with such arrays.

SUMMARY OF THE INVENTION

Improved techniques for synthesizing, hybridizing, analyzing, and sequencing nucleic acids (oligonucleotides) are provided by the present invention.

According to one embodiment of the invention, a target oligonucleotide is exposed to a large number of immobilized probes of shorter length. The probes are collectively referred to as an "array." In the method, one identifies whether a target nucleic acid is complementary to a probe in the array by identifying first a core probe having high affinity to the target, and then evaluating the binding characteristics of all probes with a single base mismatch as compared to the core probe. If the single base mismatch probes exhibit a characteristic binding or affinity pattern, then the core probe is exactly complementary to at least a portion of the target nucleic acid.

The method can be extended to sequence a target nucleic acid larger than any probe in the array by evaluating the binding affinity of probes that can be termed "left" and "right" extensions of the core probe. The correct left and right extensions of the core are those that exhibit the strongest binding affinity and/or a specific hybridization pattern of single base mismatch probes. The binding affinity characteristics of single base mismatch probes follow a characteristic pattern in which probe/target complexes with mismatches on the 3' or 5' termini are more stable than probe/target complexes with internal mismatches. The process is then repeated to determine additional left and right extensions of the core probe to provide the sequence of a nucleic acid target.

In some embodiments, such as in diagnostics, a target is expected to have a particular sequence. To determine if the target has the expected sequence, an array of probes is synthesized that includes a complementary probe and all or some subset of all single base mismatch probes. Through analysis of the hybridization pattern of the target to such probes, it can be determined if the target has the expected sequence and, if not, the sequence of the target may optionally be determined.

Kits for analysis of nucleic acid targets are also provided by virtue of the present invention. According to one embodiment, a kit includes an array of nucleic acid probes. The probes may include a perfect complement to a target nucleic acid. The probes also include probes that are single base substitutions of the perfect complement probe. The kit may include one or more of the A, C, T, G, and/or U substitutions of the perfect complement. Such kits will have a variety of uses, including analysis of targets for a particular genetic sequence, such as in analysis for genetic diseases.

A further understanding of the nature and advantages of the inventions herein may be realized by reference to the remaining portions of the specification and the attached drawings.

BRIEF DESCRIPTION OF THE DRAWINGS

FIG. 5A is a fluorescence image following hybridization of the array with a target nucleic acid (10 nM 5'-GCGGCGGC-fluorescein) in 6× SSPE, 0.1% Triton X-100 for 15 min. at 15° C. FIG. 5B is a matrix de-coder showing where each probe made during the synthesis of S-3'-CG(A+G+C+T)$^4$CG is located. The site containing the probe sequence S-3'-CGCGCCCG is shown as a dark area. The combinatorial synthesis notation used herein is fully described in U.S. application Ser. No. 07/624,120, incorporated herein by reference for all purposes.;

FIG. 6A illustrates a target hybridized to a probe on a substrate. FIGS. 6B and 6C illustrate plots of normalized binding affinity vs. mismatch position;

FIGS. 12A to 12D illustrate a process for determining the nucleotide sequence of an n-member (the number of monomers in the nucleotide) target oligonucleotide based oil hybridization results from shorter k-member probes. In particular, FIGS. 12A to 12D illustrate application of the present method to sequencing a 10-base target with 4-base probes;

FIGS. 15A and 15B illustrate wild-type and mutation analysis using single base mismatch profiles;

DESCRIPTION OF THE PREFERRED EMBODIMENTS

Contents

A. Synthesis
B. Hybridization
C. Mismatch Analysis
D. Applications
E. Conclusion Definitions Probe—A molecule of known composition or monomer sequence, typically formed on a solid surface, which is or may be exposed to a target molecule and examined to determine if the probe has hybridized to the target. A "core" probe is a probe that exhibits strong affinity for a target. An "extension" probe is a probe that includes all or a portion of a core probe sequence plus one or more possible extensions of the core probe sequence. The present application refers to "left" extensions as an extension at the 3'-end of a probe and a "right" extension refers to an extension at the 5'-end of a probe, although the opposite notation could obviously be adopted.

Target—A molecule, typically of unknown composition or monomer sequence, for which it is desired to study the composition or monomer sequence. A target may be a part of a larger molecule, such as a few bases in a longer nucleic acid.

n-Base Mismatch—A probe having n monomers therein that differ from the corresponding monomers in a core probe, wherein n is one or greater.

A, T, C, G, U—Are abbreviations for the nucleotides adenine, thymine, cytosine, guanine, and uridine, respectively.

Library—A collection of nucleic acid probes of pre-defined nucleotide sequence, often formed in one or more substrates, which are used in hybridization studies of target nucleic acids.

A. Synthesis

Figure 1:
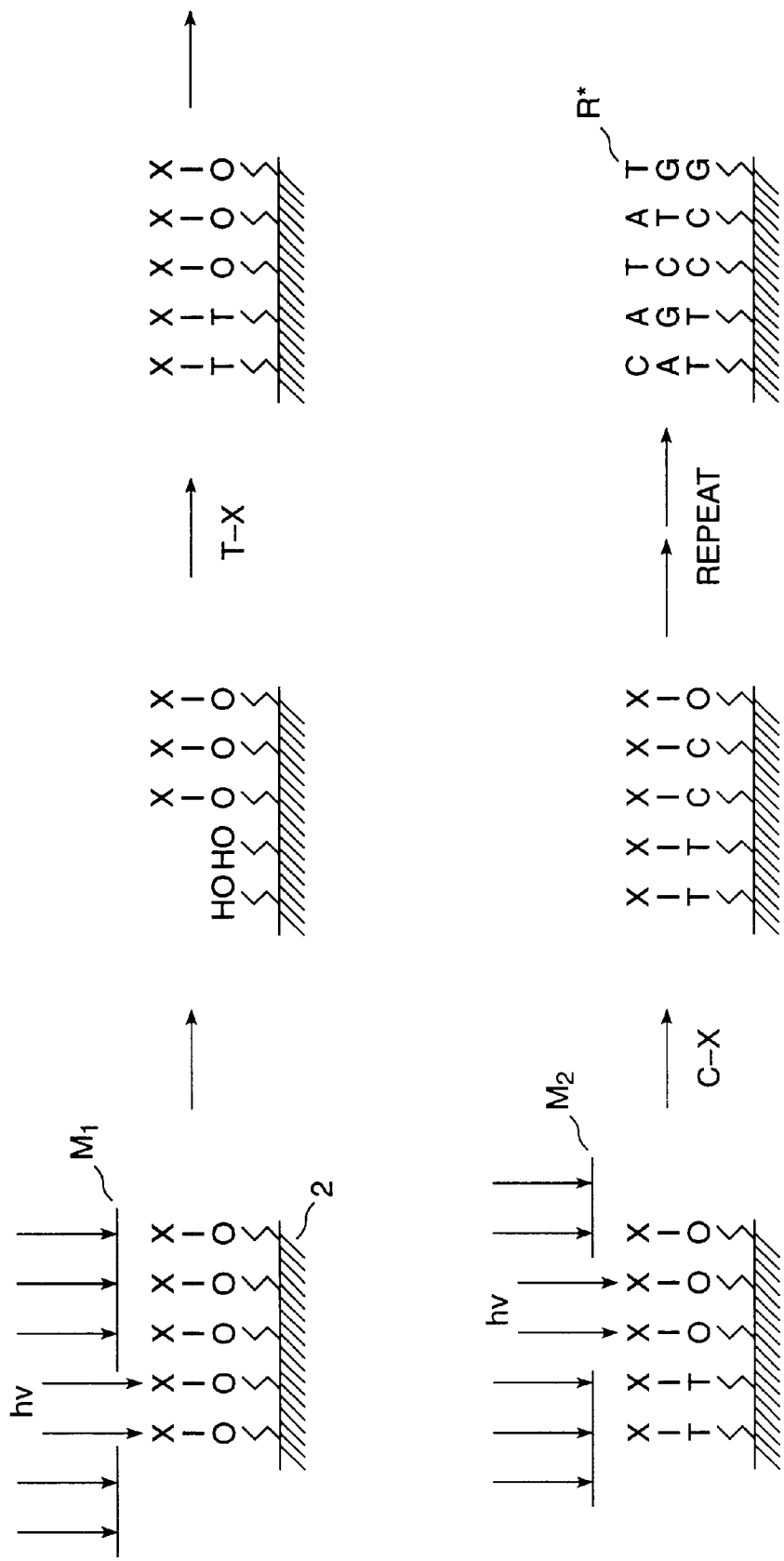
FIG. 1 illustrates light-directed synthesis of oligonucleotides. A surface (2) bearing photoprotected hydroxyls (OX) is illuminated through a photolithographic mask ($M_1$) generating free hydroxyls (OH) in the photodeprotected regions. The hydroxyl groups are then coupled to a 5'-photoprotected deoxynucleoside phosphoramidite (e.g., T-X). A new mask ($M_2$) is used to illuminate a new pattern on the surface, and a second photoprotected phosphoramidite (e.g., C-X) is then coupled. Rounds of illumination and coupling are repeated until the desired set of oligonucleotide probes is obtained. A target (R) is exposed to the oligonucleotides, optionally with a label (*). The location(s) where the target binds to the array is used to determine the sequence of the target.

A method for a light-directed oligonucleotide synthesis is depicted in FIG. 1. Such strategies are described in greater detail in U.S. Pat. No. 5,143,854, assigned to the assignee of the present inventions and incorporated herein by reference for all purposes.

In the light-directed synthesis method illustrated in FIG. 1, a surface 2 derivatized with a photolabile protecting group or groups (X) is illuminated through a photolithographic mask $M_1$ exposing reactive hydroxyl (OH) groups. The first (T-X) of a series of phosphoramidite activated nucleosides (protected at the 5'-hydroxyl with a photolabile protecting group) is then exposed to the entire surface. Coupling only occurs at the sites that were exposed to light during the preceding illumination.

After the coupling reaction is complete, the substrate is rinsed, and the surface is again illuminated through a new or translated mask $M_2$ to expose different groups for coupling. A new phosphoramidite activated nucleoside C-X (again protected at the 5'-hydroxyl with a photolabile protecting group) is added and coupled to the exposed sites. The process is repeated through cycles of photodeprotection and coupling to produce a desired set of oligonucleotide probes on the substrate. Because photolithography is used, the process can be miniaturized. Furthermore, because reactions only occur at sites spatially addressed by light, the nucleotide sequence of the probe at each site is precisely known, and the interaction of oligonucleotide probes at each site with target molecules (either target nucleic acids or, in other embodiments, proteins such as receptors) can be assessed.

Photoprotected deoxynucleosides have been developed for this process including 5'-O-(α-methyl-6-nitropiperonyloxycarbonyl)-N-acyl-2'-deoxynucleosides, or MeNPoc-N-acyl-deoxynucleosides, MeNPoc-dT, MeNPoc-$dC^{ibu}$, MeNPoc-$dG^{PAC}$, and MeNPoc-$dA^{PAC}$. Protecting group chemistry is disclosed in greater detail in PCT patent Publication No. 92/10092 and U.S. application Ser. Nos. 07/624,120, filed Dec. 6, 1990, and 07/971,181, filed Nov. 2, 1992, both assigned to the assignee of this invention and incorporated herein by reference for all purposes.

EXAMPLES

1. Protecting Groups

Because the bases have strong π-π* transitions in the 280 nm region, the deprotection wavelength of photoremovable protecting groups should be at wavelengths longer than 280 nm to avoid undesirable nucleoside photochemistry. In addition, the photodeprotection rates of the four deoxy-nucleosides should be similar, so that light will equally deprotect hydroxyls (or other functional groups, such as sulfhydryl or amino groups) in all illuminated synthesis sites.

To meet these criteria, a set of 5'-O-(α-methyl-6-nitropiperonyloxycarbonyl)-N-acyl-2'-deoxynucleosides (MeNPoc-N-acyl-deoxynucleosides) has been developed for light-directed synthesis, and the photokinetic behavior of the protected nucleosides has been measured. The synthetic pathway for preparing 5'-O'-(α-methyl-6-nitropiperonyloxycarbonyl)-N-acyl-2'-deoxynucleoside phosphoramidites is illustrated in Scheme I.

Scheme I

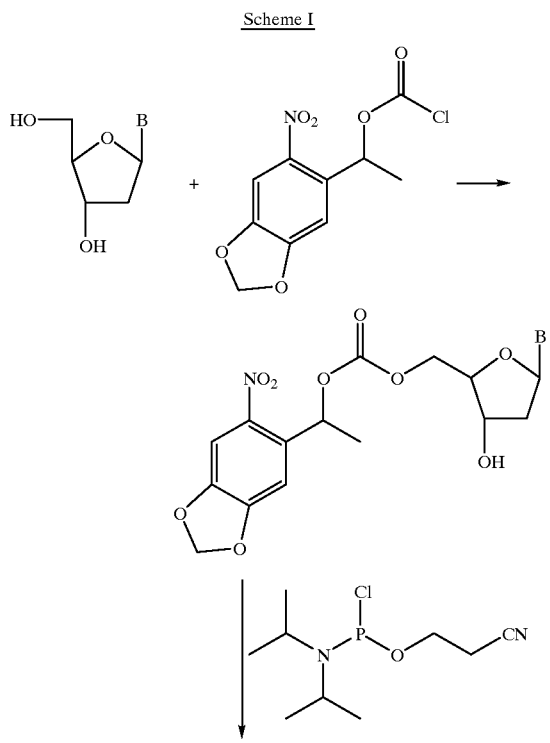

-continued

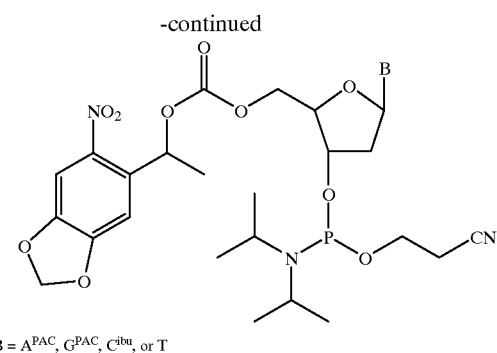

B = A$^{PAC}$, G$^{PAC}$, C$^{ibu}$, or T

In the first step, an N-acyl-2'-deoxynucleoside was reacted with 1-(2-nitro-4,5-methylenedioxyphenyl)-ethan-1-chloroformate to yield 5'-MeNPoc-N-acyl-2'-deoxynucleoside. In the second step, the 3'-hydroxyl was reacted with 2-cyanoethyl-N,N'-diisopropylchlorophosphoramidite using standard procedures to yield the 5'-MeNPoc-N-acyl-2'-deoxynucleoside-3'-O-diisopropylchlorophosphoramidites. These reagents were stable for long periods when stored dry under argon at 4° C.

A 0.1 mM solution of each of the four deoxynucleosides, MeNPoc-dT, MeNPoc-dC$^{ibu}$, MeNPoc-dG$^{PAC}$, and MeNPoc-dA$^{PAC}$ was prepared in dioxane. Aliquots (200 mL) were irradiated with 14.5 mW/cm$^2$ 365 nm light in a narrow path (2 mm) quartz cuvette for various times. Four or five time points were collected for each base, and the solutions were analyzed for loss of starting material with an HPLC system at 280 nm and a nucleosil 5-C$_8$ HPLC column, eluting with a mobile phase of 60% (v/v) in water containing 0.1% (v/v) TFA (MeNPoc-dT required a mobile phase of 70% (v/v) methanol in water). Peak areas of the residual MeNPoc-N-acyl-deoxynucleoside were calculated, yielding photolysis half-times of 28 s, 31 s, 27 s, and 18 s for MeNPoc-dT, MeNPoc-dC$^{ibu}$, MeNPoc-dG$^{PAC}$, and MeNPoc-dA$^{PAC}$, respectively. In subsequent lithographic experiments, illumination times of 4.5 min. ($9*t_{1/2}^{MeNPoc-dC}$) led to more than 99% removal of MeNPoc protecting groups.

In a light-directed synthesis, the overall synthesis yield depends on the photodeprotection yield, the photodeprotection contrast, and the chemical coupling efficiency. Photokinetic conditions are preferably chosen to ensure that photodeprotection yields are over 99%. Unwanted photolysis in normally dark regions of the substrate can adversely affect the synthesis fidelity but can be minimized by using lithographic masks with a high optical density (5 ODU) and by careful index matching of tie optical surfaces. Condensation efficiencies of DMT-N-acyl-deoxynucleoside phosphoramidites to the glass substrates have been measured in the range of 95% to 99%. The condensation efficiencies of the MeNPoc-N-acyl-deoxynucleoside phosphoramidites have also been measured at greater than 90%, although the efficiencies can vary from synthesis to synthesis and should be monitored.

2. Coupling Efficiency Measurements

To investigate the coupling efficiencies of the photoprotected nucleosides, each of the four MeNPoc-amidites was first coupled to a substrate (via DMT chemistry). A region of the substrate was illuminated, and a MeNPoc-phosphoramidite was added without a protective group. A new region of the substrate was then illuminated; a fluorescent deoxynucleoside phosphoramidite (FAM-phosphoramidite Applied Biosystems) was coupled; and the substrate was scanned for signal. If the fluorescently labeled phosphoramidite reacts at both the newly exposed hydroxyl groups and the previously unreacted hydroxyl groups, then the ratio of fluorescence intensities between the two sites provides a measure of the coupling efficiency. This measurement assumes that surface photolysis yields are near unity. The chemical coupling yields using this or similar assays are variable but high, ranging between 80–95%.

In a separate assay, the chemical coupling efficiencies were measured on hexaethyleneglycol derivatized substrate. First, a glycol linker was detritylated and a MeNPoc-deoxynucleoside-O-cyanoethylphosphoramidite coupled to the resin without capping. Next, a DMT-deoxucleoside-cyanoethylphosphoramidite (reporter-amidite) was coupled to the resin. The reporter-amidite couples to any unreacted hydroxyl groups from the first step. The trityl effluents were collected and quantified by absorption spectroscopy. Effluents were also collected from the lines immediately after the MeNPoc-phosphoramidite coupling to measure residual trityl left in the delivery lines. In this assay, the coupling efficiencies are measured assuming a 100% coupling efficiency of the reporter-amidite. The coupling efficiencies of the MeNPoc-deoxyribonucleoside-O-cyanoethylphosphoramidites to the hexaethyleneglycol linker and the efficiencies of the sixteen dinucleotides were measured and were indistinguishable from DMT-deoxynucleoside phosphoramidites.

3. Spatially Directed Synthesis of an Oligonucleotide Probe

To initiate the synthesis of an oligonucleotide probe, substrates were prepared, and MeNPoc-dC$^{ibu}$-3'-O-phosphoramidite was attached to a synthesis support through a synthetic linker. Regions of the support were activated for synthesis by illumination through 800×1280 μm apertures of a photolithographic mask. Seven additional phosphoramidite synthesis cycles were performed (with the corresponding DMT protected deoxynucleosides) to generate the S-3'-CGCATCCG. Following removal of the phosphate and exocyclic amine protecting groups with concentrated NH$_4$OH for 4 hours at room temperature, the substrate was mounted in a water jacketed thermostatically controlled hybridization chamber. This substrate was used in the mismatch experiments referred to below.

B. Hybridization

Oligonucleotide arrays can be used in a wide variety of applications, including hybridization studies. In a hybridization study, the array can be exposed to a receptor (R) of interest, as shown in FIG. 1. The receptor can be labelled with an appropriate label (*), such as fluorescein. The locations on the substrate where the receptor has bound are determined and, through knowledge of the sequence of the oligonucleotide probe at that location one can then determine, if the receptor is an oligonucleotide, the sequence of the receptor.

Sequencing by hybridization (SBH) is most efficiently practiced by attaching many probes to a surface to form an array in which the identity of the probe at each site is known. A labeled target DNA or RNA is then hybridized to the array, and the hybridization pattern is examined to determine the identity of all complementary probes in the array. Contrary to the teachings of the prior art, which teaches that mismatched probe/target complexes are not of interest, the present invention provides an analytical method in which the hybridization signal of mismatched probe/target complexes identifies or confirms the identity of the perfectly matched probe/target complexes on the array.

Arrays of oligonucleotides are efficiently generated for the hybridization studies using light-directed synthesis techniques. As discussed below, an array of all tetranucleotides was produced in sixteen cycles, which required only 4 hours to complete. Because combinatorial strategies are used, the number of different compounds on the array increases exponentially during synthesis, while the number of chemical coupling cycles increases only linearly. For example, expanding the synthesis to the complete set of $4^8$ (65,536) octanucleotides adds only 4 hours (or less) to the synthesis due to the 16 additional cycles required. Furthermore, combinatorial synthesis strategies can be implemented to generate arrays of any desired probe composition. For example, because the entire set of dodecamers ($4^{12}$) can be produced in 48 photolysis and coupling cycles or less ($b^n$ compounds requires no more than b×n cycles), any subset of the dodecamers (including any subset of shorter oligonucleotides) can be constructed in 48 or fewer chemical coupling steps. The number of compounds in an array is limited only by the density of synthesis sites and the overall array size. The present invention has been practiced with arrays with probes synthesized in square sites 25 microns on a side. At this resolution, the entire set of 65,536 octanucleotides can be placed in an array measuring only 0.64 cm². The set of 1,048,576 dodecanucleotides requires only a 2.56 cm² array at this individual probe site size.

The success of genome sequencing projects depends on efficient DNA sequencing technologies. Current methods are highly reliant on complex procedures and require substantial manual effort. SBH offers the potential for automating many of the manual efforts in current practice. Light-directed sytnhesis offers an efficient means for large scale production of miniaturized arrays not only for SBH but for many other applications as well.

Although oligonucleotide arrays can be used for primary sequencing applications, many diagnostic methods involve the analysis of only a few nucleotide positions in a target nucleic acid sequence. Because single base changes cause multiple changes in the hybridization pattern of the target on a probe array, the oligonucleotide arrays and methods of the present invention enable one to check the accuracy of previously elucidated DNA sequences, or to scan for changes or mutations in certain specific sequences within a target nucleic acid. The latter as is important, for example, for genetic, disease, quality control, and forensic analysis. With an octanucleotide probe set, a single base change in a target nucleic acid can be detected by the loss of eight perfect hybrids, and the generation of eight new perfect hybrids. The single base change can also be detected through altered mismatch probe/target complex formation on the array. Perhaps even more surprisingly, such single base changes in a complex nucleic acid dramatically alter the overall hybridization pattern of the target to the array. According to the present invention such changes in the overall hybridization pattern are used to actually simplify the analysis.

The high information content of light-directed oligonucleotide arrays greatly benefits genetic diagnostic testing. Sequence comparisons of hundreds to thousands of different mutations can be assayed simultaneously instead of in a one-at-a-time format. Arrays can also be constructed to contain genetic markers for the rapid identification of a wide variety of pathogenic organisms, and to study the sequence specificity of RNA/RNA, RNA/DNA, protein/RNA or protein/DNA, interactions. One can use non Watson-Crick oligonucleotides and novel synthetic nucleoside analogs for antisense, triple helix, or other applications. Suitably protected RNA monomers can be employed for RNA synthesis, and a wide variety of synthetic and non-naturally occurring nucleic acid analogues can be used, depending upon the motivations of the practitioner. See, e.g., PCT patent Publication Nos. 91/19813, 92/05285, and 92/14843, incorporated herein by reference. In addition, the oligonucleotide arrays can be used to deduce thermodynamic and kinetic rules governing the formation and stability of oligonucleotide complexes.

EXAMPLES

1. Hybridization of Targets to Surface Oligonucleotides

Figure 2:
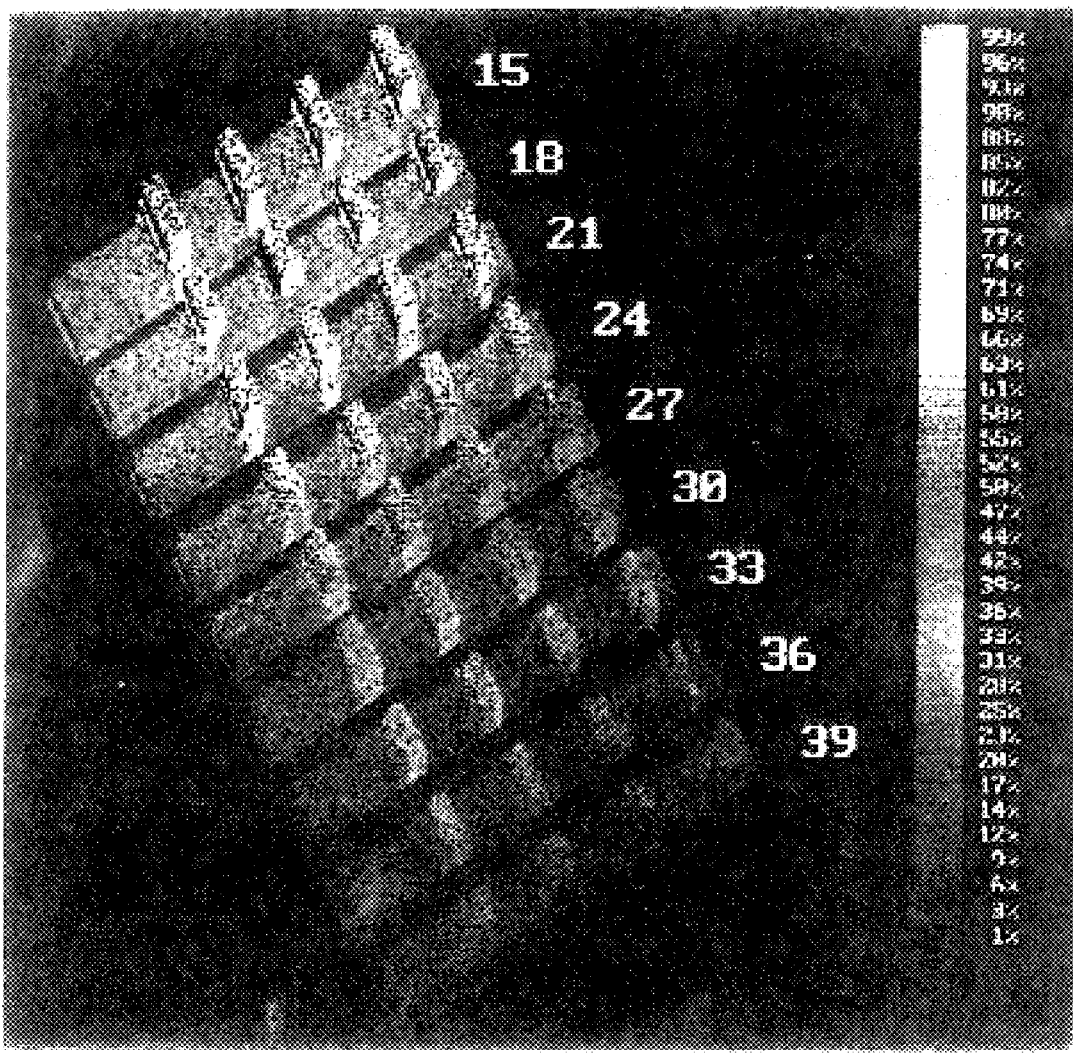
FIG. 2 illustrates hybridization and thermal dissociation of oligonucleotides, showing a fluorescence scan of a target nucleic acid (5'-GCGTAGGC-fluorescein) hybridized to an array of probes. The substrate surface was scanned with a Zeiss Axioscop 20 microscope using 488 nm argon ion laser excitation. The fluorescence emission above 520 nm was detected using a cooled photomultiplier (Hamamatsu 934-02) operated in photon counting mode. The signal intensity is indicated on the scale shown to the right of the image. The temperature is indicated to the right of each panel in ° C.

The support bound octanucleotide probes discussed above were hybridized to a target of 5'GCGTAGGC-fluorescein in the hybridization chamber by incubation for 15 minutes at 15° C. The array surface was then interrogated with an epifluorescence microscope (488 nm argon ion excitation). The fluorescence image of this scan is shown in FIG. 2. The fluorescence intensity pattern matches the 800×1280 µm stripe used to direct the synthesis of the probe. Furthermore, the signal intensities are high (four times over the background of the glass substrate), demonstrating specific binding of the target to the probe.

The behavior of the target-probe complex was investigated by increasing the temperature of the hybridization solution. After a 10 minute equilibration at each temperature, the substrate was scanned for signal. The duplex melted in the temperature range expected for the sequence under study ($T_m \approx 28°$ C. obtained from the rule $T_m = [2°(A+T)+4°(G+C)]$). The probes in the array were stable to temperature denaturation of the target-probe complex as demonstrated by rehybridization of target DNA.

2. Sequence Specificity of Target Hybridization

Figure 3:
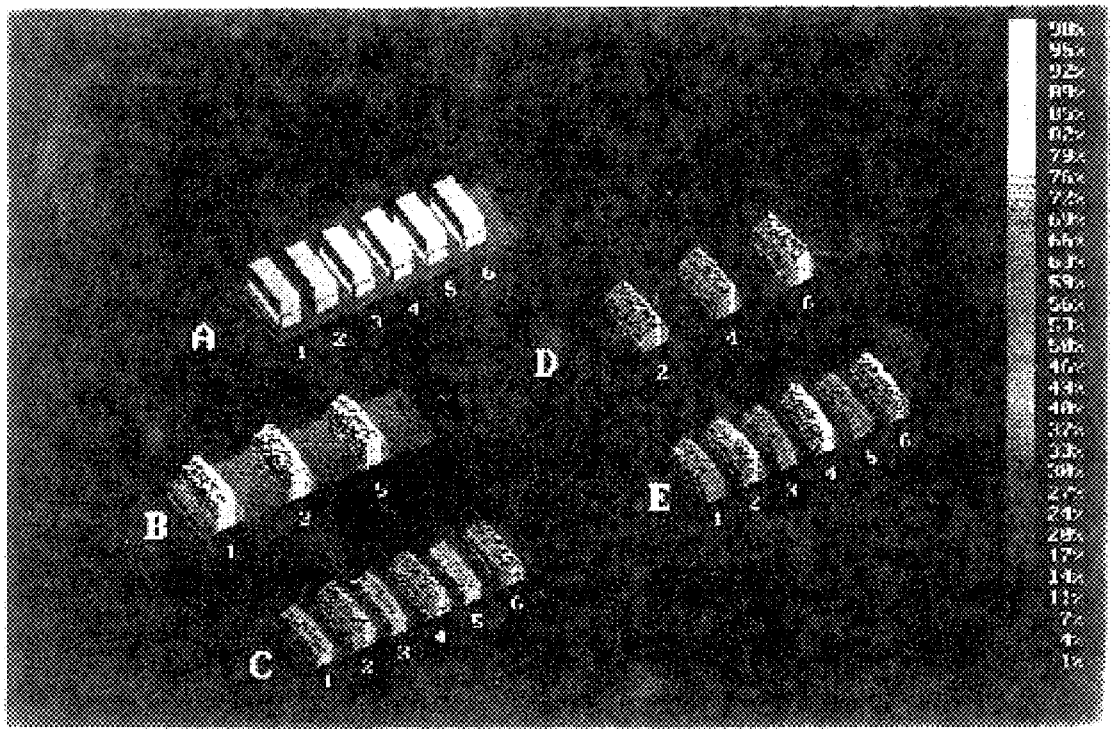
FIG. 3 illustrates the sequence specificity of hybridization. (A) is an index of the probe composition at each synthesis site. 3'-CGCATCCG surface immobilized probe (referred to herein as S-3'-CGCATCCG) was synthesized in stripes 1, 3, and 5, and the probe S-3'-CGCTTCCG was synthesized in stripes 2, 4, and 6. (B) is a fluorescence image showing hybridization of the substrate with a target nucleic acid (10 nM 5'-GCGTAGGC-fluorescein). Hybridization was performed in 6× SSPE, 0.1% Triton X-100 at 15° C. for 15 min. (C) is a fluorescence image showing hybridization with a second nucleic acid (10 nM 5'-GCGAAGGC) added to the hybridization solution of (B). (D) is a fluorescence image showing hybridization results after (1) high temperature dissociation of fluoresceinated targets from (C); and (2) incubation of the substrate with a target nucleic acid (10 nM 5'-GCGAAGGC) at 15° C. for 15 min. (E) is a fluorescence image showing hybridization with a second nucleic acid (10 nM 5'-GCGTAGGC) added to the hybridization solution of (D)

To demonstrate the sequence specificity of target hybridization, two different probes were synthesized in 800×1280 µm stripes. FIG. 3A identifies the location of the two probes. The probe S-3'-CGCATCCG was synthesized in stripes 1, 3 and 5. The probe S-3'-CGCTTCCG was synthesized in stripes 2, 4 and 6. FIG. 3B shows the results of hybridizing a 5'-GCGTAGGC-fluorescein target to the substrate at 15° C. Although the probes differ by only one internal base, the target hybridizes specifically to its complementary sequence (~500 counts above background in stripes 1, 3 and 5) with little or no detectable signal in positions 2, 4 and 6 (~10 counts). FIG. 3C shows the results of hybridization with targets to both sequences. The signal in all positions in FIG. 3C illustrates that the absence of signal in FIG. 3B is due solely to the instability of the single base mismatch. Although the targets are present in equimolar concentrations, the ratio of signals in stripes 2, 4 and 6 in FIG. 3B are approximately 1.6 times higher than the signals in regions 1, 3 and 5. This duplex has a slightly higher predicted $T_m$ than the duplex comprising regions 2, 4 and 6. The duplexes were dissociated by raising the temperature to 45° C. for 15 minutes, and the hybridizations were repeated in the reverse order (FIGS. 3D and 3E), demonstrating specificity of hybridization in the reverse direction.

Figure 4:
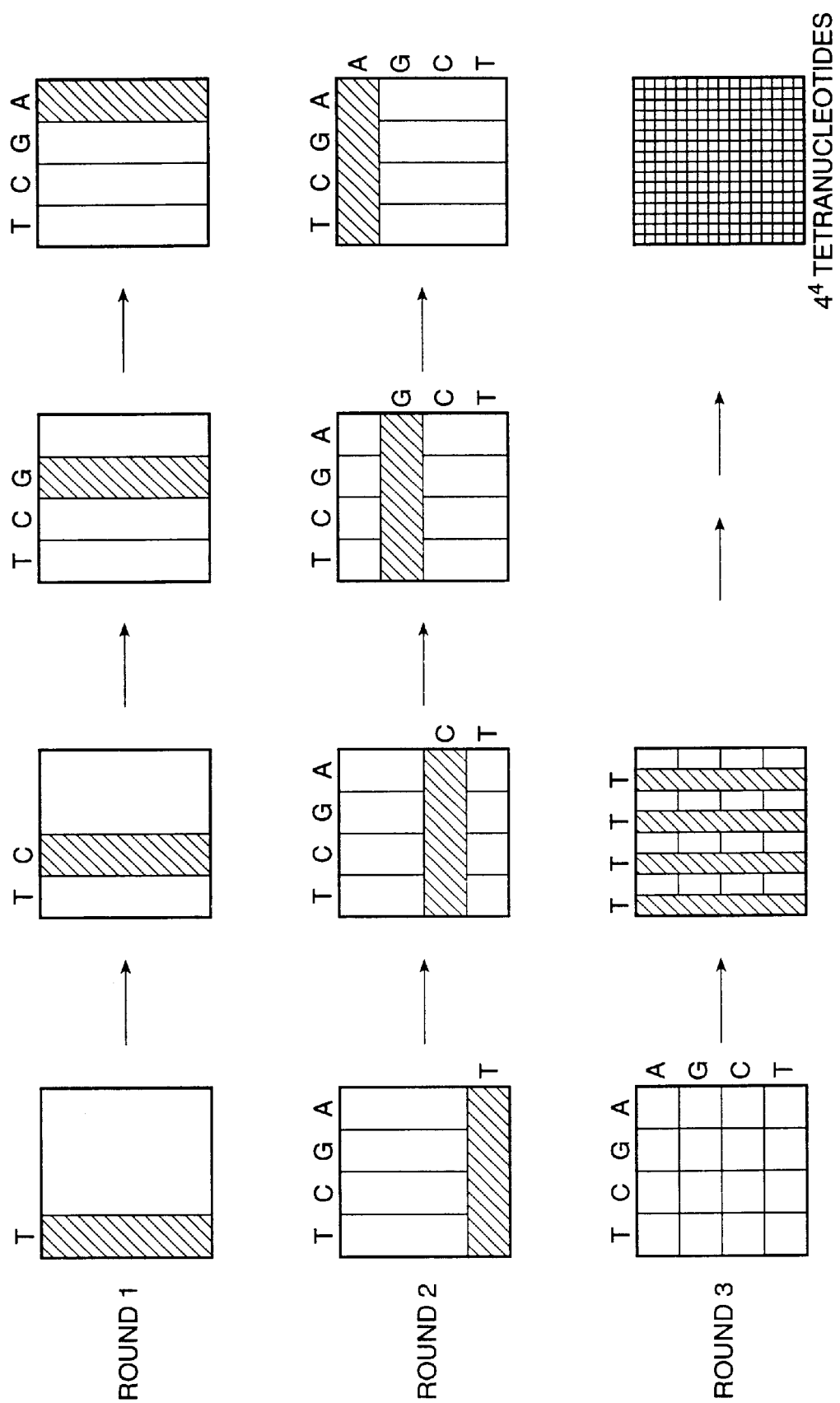
FIG. 4 illustrates combinatorial synthesis of $4^4$ tetranucleotides. In round 1, one-fourth of the synthesis area is activated by illumination through mask 1 for coupling of the first MeNPoc-nucleoside (T in this case). In cycle 2 of round 1, mask 2 activates a different one quarter section of the synthesis substrate, and a different nucleoside (C) is coupled. Further lithographic subdivisions of the array and chemical couplings generate the complete set of 256 tetranucleotides.

3. Combinatorial Synthesis of, and Hybridization of a Nucleic Acid Target to, a Probe Matrix In a light-directed synthesis, the location and composition of products depends on the pattern of illumination and the order of chemical coupling reagents (see Fodor et al., *Science* (1991) 251:767–773, for a complete description). Consider the synthesis of 256 tetranucleotides, as illustrated in FIG. 4. Mask 1 activates one fourth of the substrate surface for coupling with the first of four nucleosides in the first round of synthesis. In cycle 2, mask 2 activates a different quarter of the substrate for coupling with the second nucleoside. The process is continued to build four regions of mononucleotides. The masks of round 2 are perpendicular to those of round 1, and each cycle of round 2 generates four new dinucleotides. The process continues through round 2 to form sixteen dinucleotides as illustrated in FIG. 4. The masks of round 3 further subdivide the synthesis regions so that each coupling cycle generates 16 trimers. The subdivision of the substrate is continued through round 4 to form the tetranucleotides. The synthesis of this probe matrix can be compactly represented in polynomial notation as $(A+C+G+T)^4$. Expansion of this polynomial yields the 256 tetranucleotides.

Figure 5A:
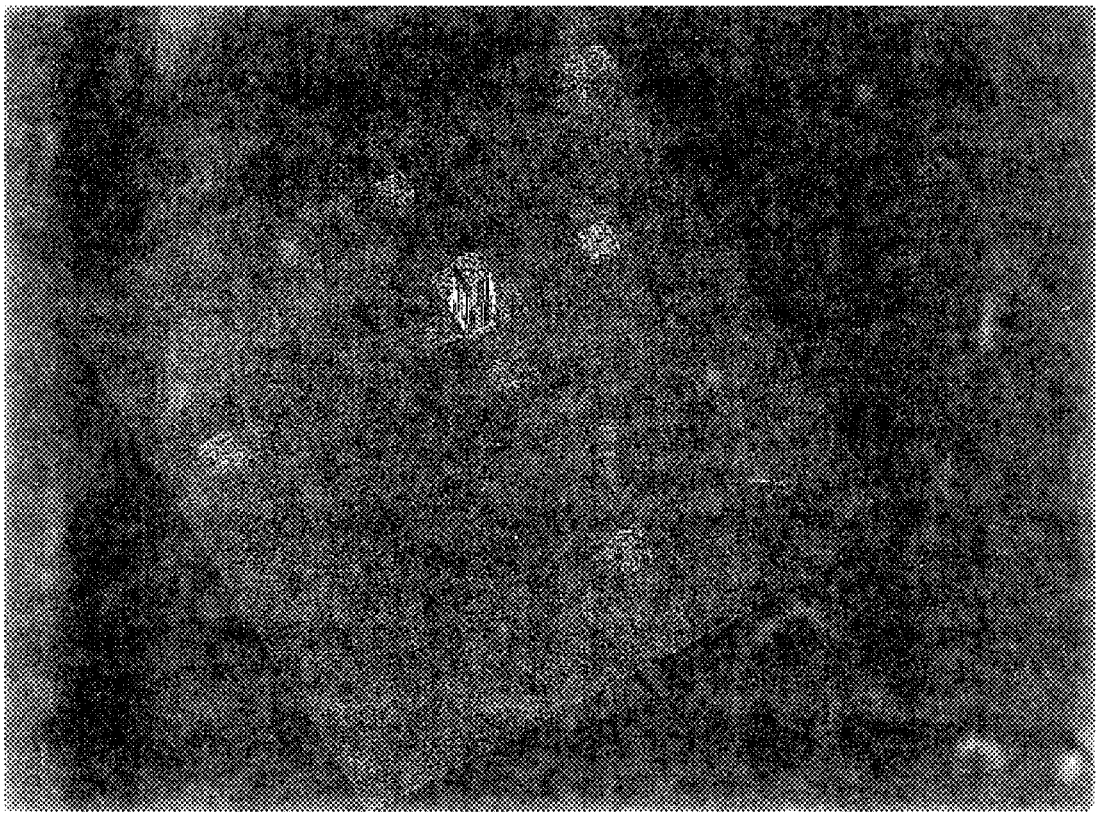
FIGS. 5A and 5B illustrate hybridization to an array of 256 octanucleotides.
Figure 5B:
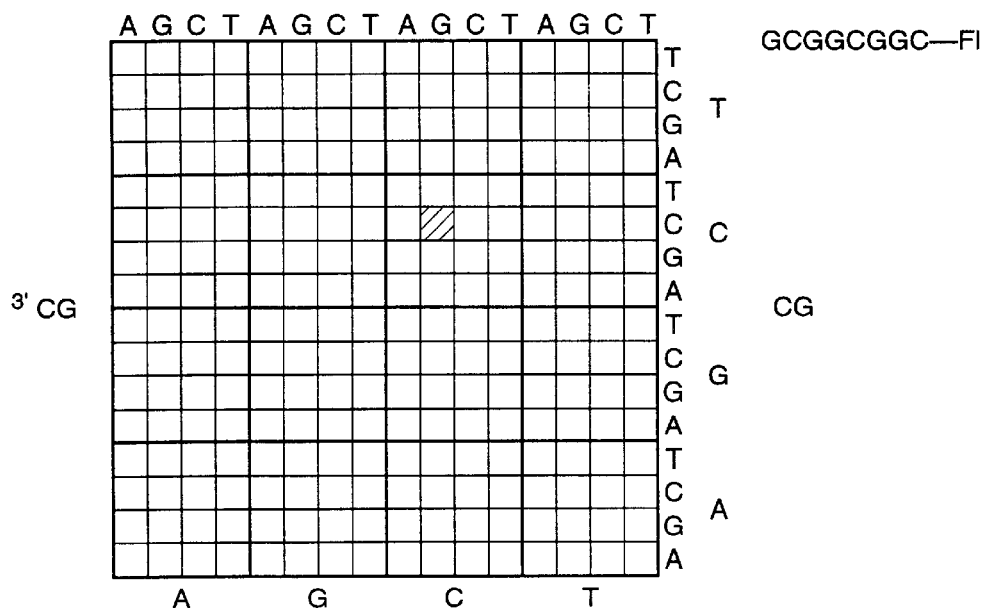

The application of an array of 256 probes synthesized by light-directed combinatorial synthesis to generate a probe matrix is illustrated in FIG. 5A. The polynomial for this synthesis is given by: 3'-CG$(A+G+C+T)^4$CG. The synthesis map is given in FIG. 5B. All possible tetranucleotides were synthesized flanked by CG at the 3'- and 5'-ends. Hybridization of target 5'-GCGGCGGC-fluorescein to this array at 15° C. correctly yielded the S-3'-CGCCGCCG complementary probe as the most intense position (2,698 counts). Significant intensity was also observed for the following mismatches: S-3'-CGCAGCCG (554 counts), S-3'-CGCCG ACG (317 counts), S-3'-CGCCGTCG (272 counts), S-3'-CG ACGCCG (242 counts), S-3'-CGTCGCCG (203 counts), S-3'-CGCCCCG (180 counts), S-3'-CGCTGCCG (163 counts), S-3'-CGCCACCG (125 counts), and S-3'-CGCC TCCG (78 counts).

C. Mismatch Analysis

The arrays discussed above can be utilized in the present method to determine the nucleic acid sequence of an oligonucleotide of length n using an array of probes of shorter length k. FIG. 6 illustrates a simple example. The target has a sequence 5'-XXYXY-3', where X and Y are complementary nucleic acids such as A and T or C and G. For discussion purposes, the illustration in FIG. 6 is simplified by using only two bases and very short sequences, but the technique can easily be extended to larger nucleic acids with, for example, all 4 RNA or DNA bases.

The sequence of the target is, generally, not known ab initio. One can determine the sequence of the target using the present method with an array of shorter probes. In this example, an array of all possible X and Y 4-mers is synthesized and then used to determine the sequence of a 5-mer target.

Initially, a "core" probe is identified. The core probe is exactly complementary to a sequence in the target using the mismatch analysis method of the present invention. The core probe is identified using one or both of the following criteria:

1. The core probe exhibits stronger binding affinity to the target than other probes, typically the strongest binding affinity of any probe in the array (that has not been identified as a core probe in a previous cycle of analysis).

2. Probes that are mismatched with the target, as compared to the core probe sequence, exhibit a characteristic pattern, discussed in greater detail below, in which probes that mismatch at the 3'- and 5'-end of the probe bind more strongly to the target than probes mismatched with the target.

Figure 6A:
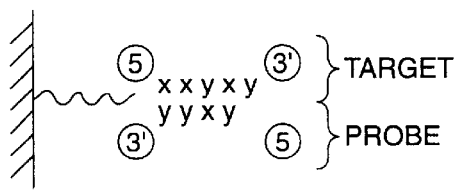
FIGS. 6A to 6C illustrate a technique for sequencing a n-mer target using k-mer probes.

In this particular example, selection criteria #1 identifies a core 4-mer probe with the strongest binding affinity to the target that has the sequence 3'-YYXY, as shown in FIG. 6A, where the probe is illustrated as having hybridized to the target. The probe 3'-YYXY (corresponding to the 5'-XXYX position of the target) is, therefore, chosen as the "core" probe.

Selection criteria #2 is utilized as a "check" to ensure the core probe is exactly complementary to the target nucleic acid. The second selection criteria evaluates hybridization data (such as the fluorescence intensity of a labeled target hybridized to an array of probes on a substrate, although other techniques are well known to those of skill in the art) of probes that have single base mismatches as compared to the core probe. In this particular case, the core probe has been selected as S-3'-YYXY. The single base mismatched probes of this core probe are: S-3'-XYXY, S-3'-YXXY, S-3'-YYYY, and S-3'-YYXX. The binding affinity characteristics of these single base mismatches are utilized to ensure that a "correct" core has been selected, or to select the core probe from among a set of probes exhibiting similar binding affinities.

Figure 6B:
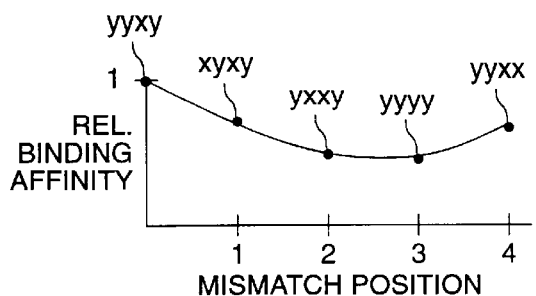

An illustrative, hypothetical plot of expected binding affinity versus mismatch position is provided in FIG. 6B. The binding affinity values (typically fluorescence intensity of labeled target hybridized to probe, although many other factors relating to affinity may be utilized) are all normalized to the binding affinity of S-3'-YYXY to the target, which is plotted as a value of 1 on the left hand portion of the graph. Because only two nucleotides are involved in this example, the value plotted for a probe mismatched at position 1 (the nucleotide at the 3'-end of the probe) is the normalized binding affinity of S-3'-XYXY. The value plotted for mismatch at position 2 is the normalized affinity of S-3'-YXXY. The value plotted for mismatch at position 3 is the normalized affinity of S-3'-YYYY, and the value plotted for mismatch position 4 is the normalized affinity of S-3'-YYXX. As noted above, "affinity" may be measured in a number of ways including, for example, the number of photon counts from fluorescence markers on the target.

The affinity of all three mismatches is lower than the core in this illustration. Moreover, the affinity plot shows that a mismatch at the 3'-end of the probe has less impact than a mismatch at the 5'-end of the probe in this particular case, although this may not always be the case. Further, mismatches at the end of the probe result in less disturbance than mismatches at the center of the probe. These features, which result in a "smile" shaped graph when plotted as shown in FIG. 6B, will be found in most plots of single base mismatch after selection of a "correct" core probe, or after accounting for a mismatched probe that is a core probe with respect to another portion of the target sequence. This information will be utilized in either selecting the core probe initially or in checking to ensure that an exactly matched core probe has been selected. Of course, in certain situations, as noted in Section B above, identification of a core is all that is required such as in, for example, forensic or genetic studies, and the like.

Figure 6C:
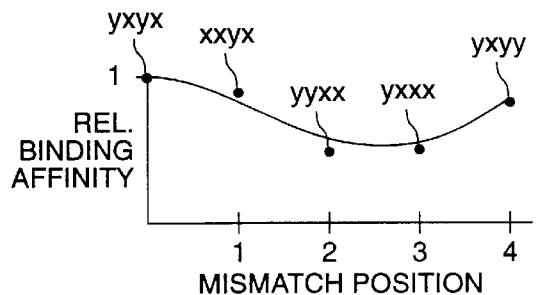

In sequencing studies, this process is then repeated for left and/or right extensions of the core probe. In the example illustrated in FIG. 6, only right extensions of the core probe are possible. The possible 4-mer extension probes of the core probe are 3'-YXYY and 3'-YXYX. Again, the same selection criteria are utilized. Between 3'-YXYY and 3'-YXYX, it would normally be found that 3'-YXYX would have the strongest binding affinity, and this probe is selected as the correct probe extension. This selection may be confirmed by again plotting the normalized binding affinity of probes with single base mismatches as compared to the core probe. A hypothetical plot is illustrated in FIG. 6C. Again, the characteristic "smile" pattern is observed, indicating that the "correct" extension has been selected, i.e., 3'-YXYX. From this information, one would correctly conclude that the sequence of the target is 5'-XXYXY.

EXAMPLES

1. (A+T)⁸ Array and Single Base Mismatch Stabilities

Figure 7:
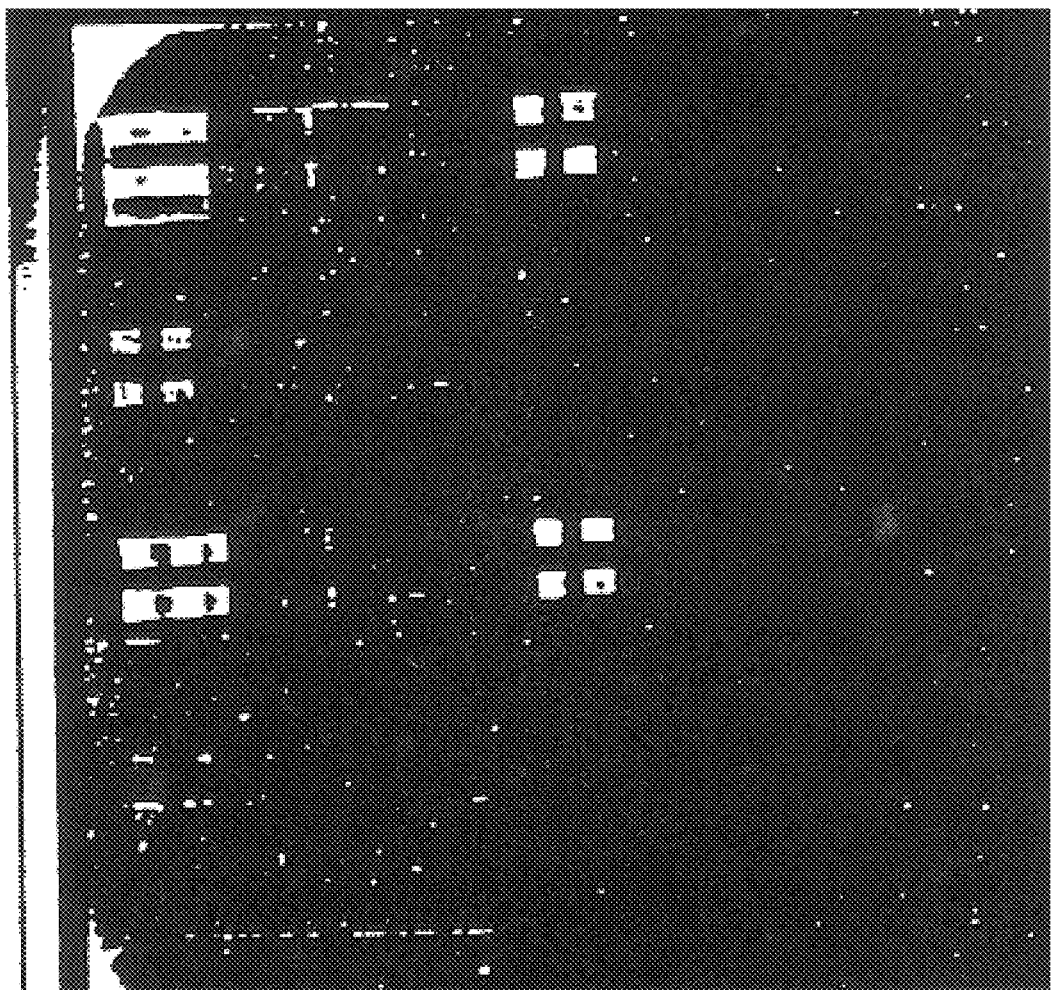
FIG. 7 illustrates a fluorescence image of a hybridization experiment.

A 20-step, 4-replica combinatorial synthesis was performed using MenPoc-dA and MenPoc-dT. The lithographic masks were chosen such that each member of a set of 256 octanucleotides was synthesized in four separate locations on the 1.28×1.28 cm array, yielding 1024 different synthesis sites, each containing an octanucleotide probe, each site 400×400 μm in size. Following synthesis and phenoxyacetyl deprotection of the dA amine, the substrate was mounted in a thermostatically regulated staining and flow cell, incubated with 1 nM 5'-AAAAAAAA-fluorescein at 15° C., and then scanned in a Zeiss epifluorescence microscope. The resulting fluorescent image is shown in FIG. 7.

Figure 8:
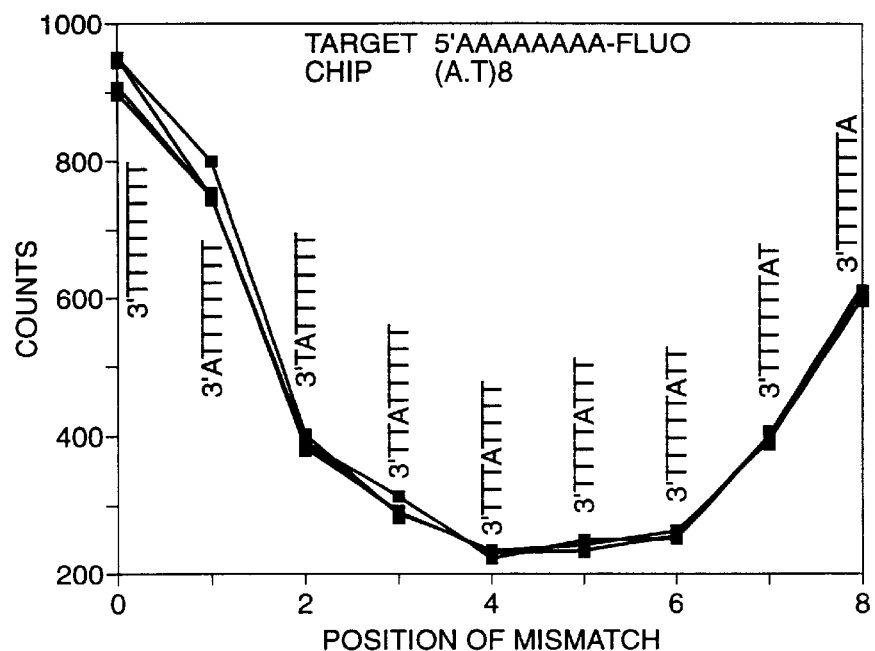
FIG. 8 illustrates hybridization events graphically as a function of singe base mismatch.

Fluorescence intensities of the hybridization events as a function of single base mismatch are provided graphically in FIG. 8. Each of the four independent intensities for each octanucleotide probe that differs from the core probe at at single base is plotted. Position zero mismatch (i.e., the perfect complement 3'-TTTTTTTT) is the brightest position on the array at ~900 counts; the background signal of this array is approximately 220 counts. Mismatch position 1 (at the 3'-end of the probe) is the next brightest at ~760 counts. A "smile" or "U" shaped curve of the following positions indicates the relative stability of the mismatches at each position of the probe/target complex. This "mismatch family" characterizes nucleic acid interaction with an array of probes and provides or confirms the identification of the target sequence. The mismatches at positions 3, 4, 5 and 6 are more destabilizing and yield intensities virtually indistinguishable from background. The mismatch at position 1 (the point where the 3'-end of the octanucleotide is tethered to the substrate) is less destablizing than the corresponding mismatch at position 8 (the free 5'-end). The uniformity of the array synthesis and the target hybridization is reflected in the low variation of intensities between the four duplicate synthesis sites.

Figure 9:
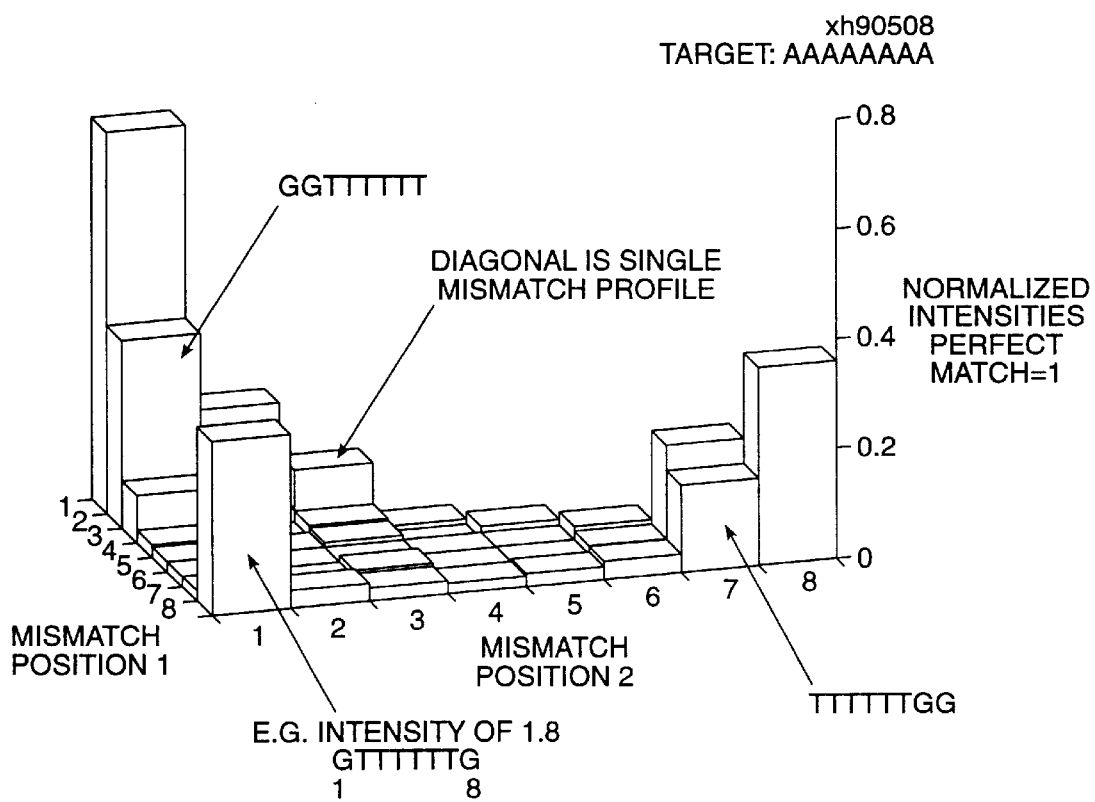
FIG. 9 illustrates fluorescence intensity as a function of pairs of mismatches.

The method of the present invention can also utilize information from target hybridization to probes with two or more mismatches. Fluorescence intensities as a function of pairs of mismatches are presented in FIG. 9. In this case, the intensity data have been normalized so that a perfect match has intensity 1. For example, the data at index 1,8 corresponds to mismatches at each end of the probe/target duplex. The diagonal (index 1,1 to 8,8) corresponds to the single mismatches illustrated in FIG. 8. The highest intensities correspond to single and pairs of mismatches at the ends of the probe/target complex.

2. (G+T)⁸ Array and Sequence Reconstruction

An octanucleotide array of MenPoc-dG and MenPoc-dT was synthesiszed. The format of the synthesis was similar to that for the (A+T)⁸ array, discussed above, and resulted in 256 octanucleotides of G and T in replicates of four (1024 total). After final deprotection and attachment to a temperature-controlled (15° C.) hybridization chamber, the probe array was incubated with 1 nM 5'-AACCCAAACCC-fluorescein target and scanned. The resulting image is given in FIG. 10. Four distinct but overlapping, perfectly complementary octanucleotide hybridizations are expected: 3'-TTGGGTTT, TGGGTTTG, GGGTTTGG, and GGTTTGGG. As shown herein, the moderate stablility of probe/target complexes with single base pair mismatches generates families of probes with moderate signals. A cursory inspection of the many intense features of FIG. 10 revealed a complex pattern.

Figure 10:
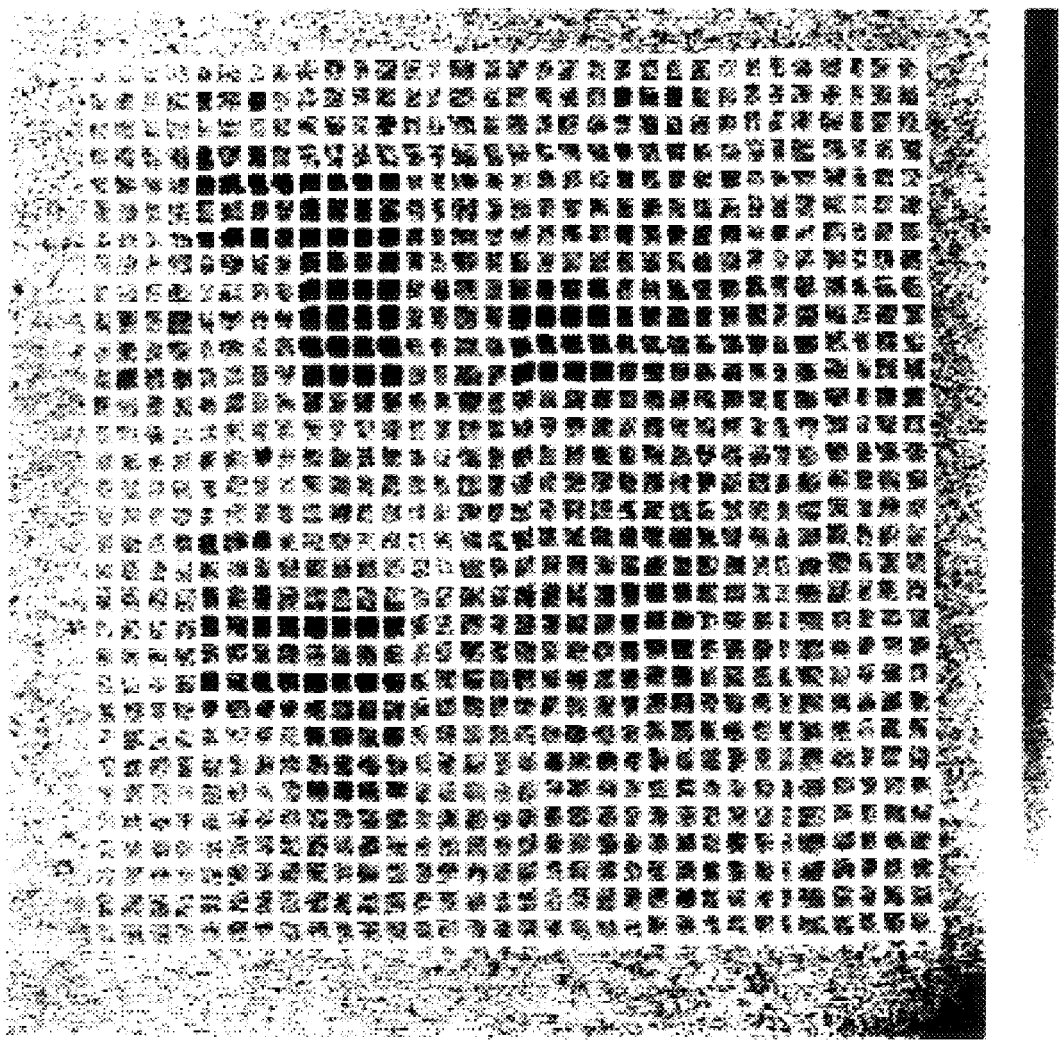
FIG. 10 illustrates a fluorescence image of a single base mismatch experiment.

The reconstruction heuristic provided by the present invention effectively utilizes the complex data pattern in FIG. 10. The algorithm assumes as a general rule that perfectly matched probe/target complexes have higher fluorescence intensities, and perfect matches and related single base mismatch typically form a profile similar to that shown in FIG. 6.

Figure 11A:
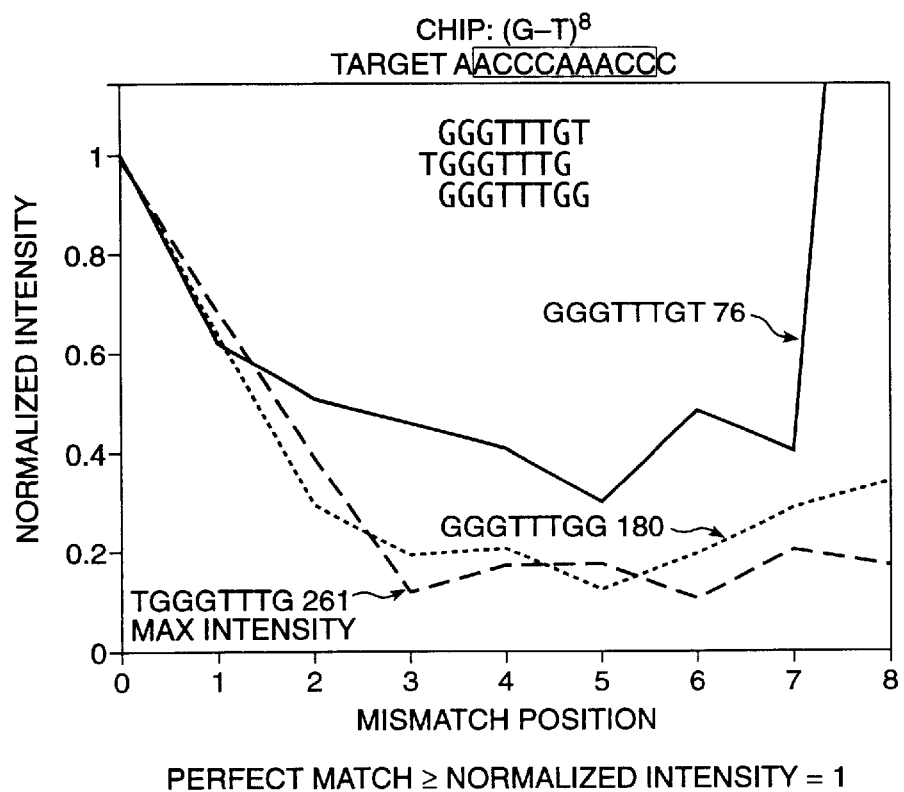
FIGS. 11A to 11C illustrate various single base mismatch profiles.
Figure 11B:
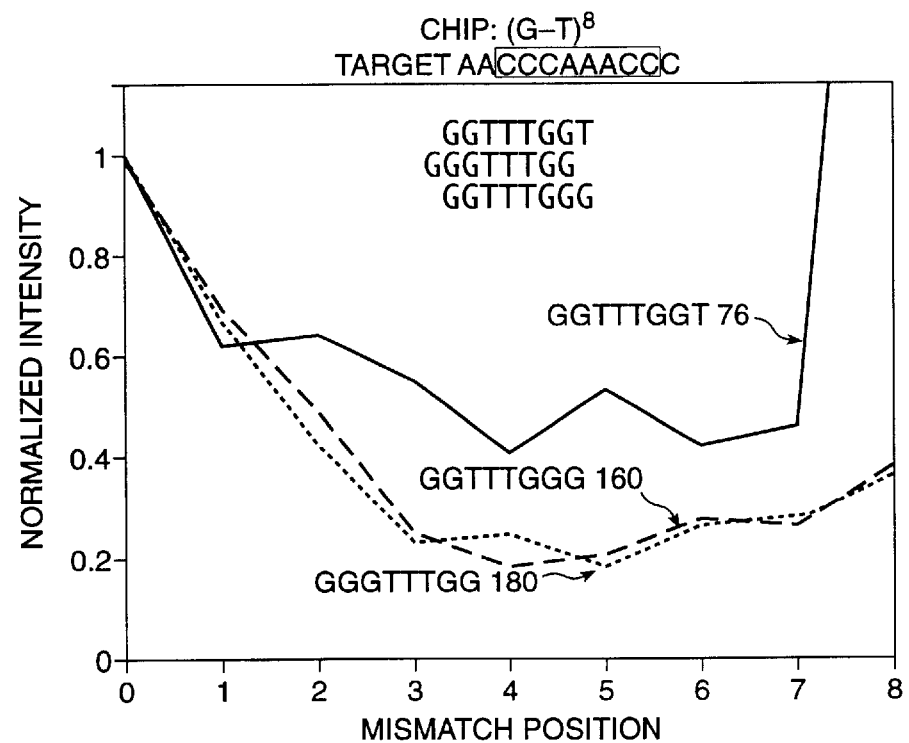
Figure 11C:
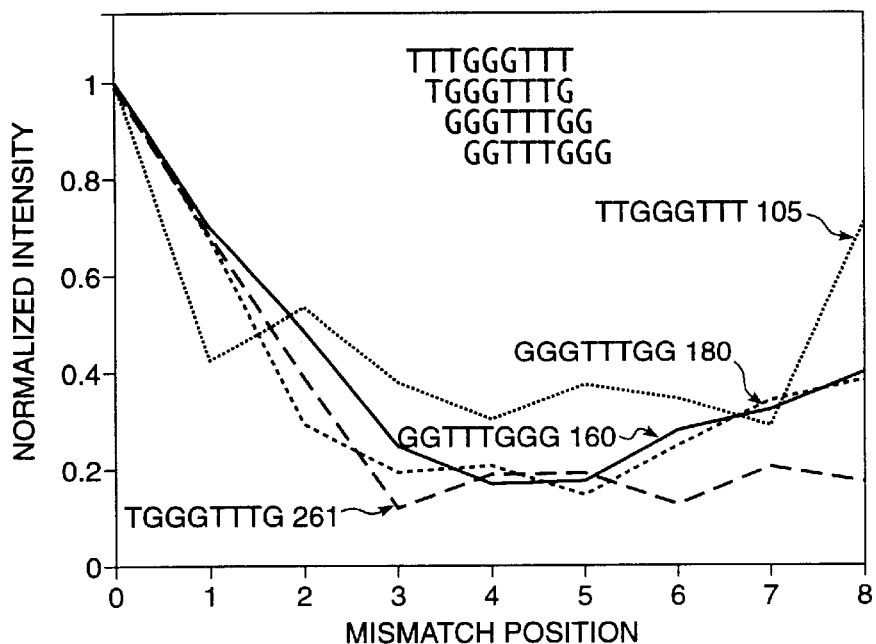

The probe with the highest intensity should be a perfect match to the target. Corresponding mismatch profiles are shown in FIGS. 11A to 11C. One first plots the mismatch profile for the probe with the highest intensity (S-3'-TGGGTTTG in this case) to verify that the probe is exactly complementary to the target. Assuming that this probe is complementary to a fragment of the target, we consider "extending" a base on the 3'-end of the target. In this case, there are two probe choices. One of the two 8-mer probes S-3'-GGGTTTGT and S-3'-GGGTTTGG, will be exactly complementary to the target nucleic acid. The mismatch profile for each of these two probes, as well as for probe S-3'-TGGGTTTG, is shown with intensity values in FIG. 11A. Note that the probe S-3'-GGGTTTGG has the mismatch profile most similar to that of probe S-3'-TGGGTTTG (a typical "smile" plot). Therefore, one will conclude that the correct extension probe is S-3'-GGGTTTGG.

FIG. 11B shows repetition of this process to evaluate the 3'-end of the target sequence. Because the probe S-3'-GGTTTGG has a smile-shaped mismatch profile most like the core S-3'-GGGTTTGG, and because the probe S-3'-GGTTTGT does not, one will correctly conclude that the probe S-3'-GGGTTTGG is the correct extension probe. This process can be repeated until neither profile has the correct shape, or the absolute intensity is well below that of the highest intensity, indicating that the "end" of the target has been reached. A similar method provides the sequence of the target extending to the 5'-end. FIG. 11C shows the mismatch curves for all the perfectly matched probes; each curve has the consistent shape predicted for this target.

Figure 12A:
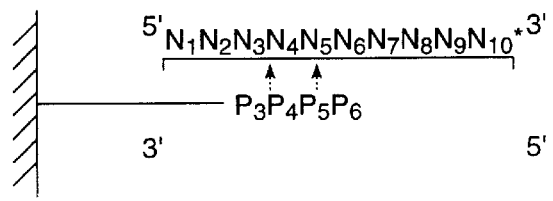

The techniques described above can of course be readily extended to nucleic acids of any length, as illustrated in the various panels of FIGS. 12A to 12D. As shown in FIG. 12A, a 10-mer target is to be sequenced, and the sequence is indicated by 5'-$N_1N_2N_3N_4N_5N_6N_7N_8N_9N_{10}$-3', where N is any nucleotide or nucleic acid monomer, and the subscript indicates the nucleotide position in the probe, with 3 indicating the 3'-end terminal monomer. Those of skill recognize that, if the probes were synthesized with the 5'-end attached to the substrate, the method of the invention can be applied with appropriate modification.

An array of shorter oligonucleotides can be used to sequence a larger nucleotide according to one aspect of the present invention. In the particular example shown in FIGS. 12A to 12D, 4-mers (oligonucleotide probes 4 monomers in length) are used to sequence the unknown 10-mer target. In practice, longer probes and targets will typically be employed, but this illustrative example facilitates understanding of the invention. A single member of the 4-mer array is shown in FIG. 12A and has the sequence S-3'-$P_3P_4P_5P_6$, where the various P (probe) nucleotides will be selected from the group of A, T, C, U, G, and other monomers, depending on the application, and the subscript indicates position relative to the target. For discussion purposes, the hybridization data are presumed to be available from a single array. However, one can utilize multiple arrays, arrays synthesized at different times, or even individual probes to practice the method. As noted, the probe length of 4 is selected to facilitate discussion; in practice, longer probes will typically be employed.

S-3'-$P_3P_4P_5P_6$ is selected as a core probe from the array due to its exhibition of a strong binding affinity to the target and a correct mismatch profile. In the array of all 4-mers, the sequence S-3'-$P_3P_4P_5P_6$ is chosen as the core sequence, because when a fluorescein-labeled target (shown as 5'-$N_1N_2N_3N_4N_5N_6N_7N_8N_9N_{10}$*-3' in FIG. 12A) is exposed to the substrate, the target hybridizes to the probe, as indicated by the arrows in FIG. 12A, and high fluorescence intensity (i.e., a large number of photon counts) is observed in the portion of the substrate containing the probe S-3'-$P_3P_4P_5P_6$, as compared to other portions of the substrate. Normally, the sequence exhibiting the strongest binding affinity will be chosen as the first core sequence.

Figure 12B:
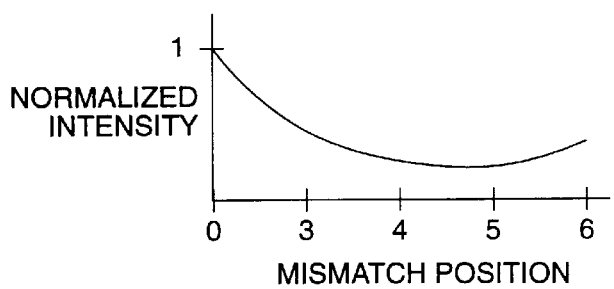

One preferably verifies whether the first selected core sequence is a perfect complement to the target by examining the fluorescence intensity of probes in the array that differ from the core probe at a single base. FIG. 12B qualitatively illustrates a typical plot of relative intensity of single base mismatches versus position of the mismatch for the S-3'-$P_3P_4P_5P_6$ core probe. As a simple example, assume that, in the sequence S-3'-$P_3P_4P_5P_6$, the nucleotide C is not present. FIG. 12B illustrates in a qualitative way the normalized fluorescence intensity of probes that differ from the core sequence probe by substitution of C into the sequence S-3'-$P_3P_4P_5P_6$ and in which none of the C-containing mismatched probes is exactly complementary to another sequence in the target. Accordingly, FIG. 12B plots the relative fluorescence intensity of the probe set:

S-3'-$CP_4P_5P_6$,
S-3'-$P_3CP_5P_6$,
S-3'-$P_3P_4CP_6$, and
S-3'-$P_3P_4P_5C$ when they are hybridized to the target, normalized to the core probe. In alternative embodiments, average curves are plotted for substitution of all the possible nucleotides at each position (the "families" of mismatched probes), or the highest intensity is plotted for each position. Thus, the 0 position on the X axis of the graph in FIG. 12B represents no substitution and shows the fluorescence intensity due to target hybridization to core probe S-3'-$P_3P_4P_5P_6$. Because all values in FIG. 12B are normalized with respect to this value, the "no substitution" case has a normalized intensity of 1. When C is substituted at the 3, 4, 5, and 6 positions, the relative intensity values are normally less, because none of these sequences are exactly complementary to the target in this example.

The relative fluorescence intensity of a probe/target complex with a mismatch at the 3'- or 5'-end is typically higher than complexes with mismatches in the center of the probe/target complex, because mismatches at the end of the probe tend to be less destabilizing than mismatches at the center of the probe/target complex. Probe/target complexes with mismatches at the 3'-end of the probes may impact hybridization less (and thus have a higher fluorescence intensity) than those with mismatches at the 5'-end of the probes, presumably due to the proximity of the 3'-end of the probe to the substrate surface in this embodiment. Therefore, a curve plotting a normalized factor related to binding affinity versus mismatch position, tends to have the shape of a "crooked smile," as shown in FIG. 12B.

Using this methodology, one can extend a core sequence by examining probes on the array that have the same sequence as the core probe except for having been extended at one end and optionally shortened at the other. These probes are evaluated as candidate second core sequences to determine which probes are perfectly hybridized to the target. By repetition of this process, one can determine the complete nucleotide sequence of the target.

To illustate the method, FIG. 12C shows the 4 possible, 4-member "left extensions" of the core probe S-3'-$P_3P_4P_5P_6$.

As shown, the nucleotide adjacent to the sequence of the target complementary to S-3'-$P_3P_4P_5P_6$ is either A, T, C, or G, or there is no adjacent nucleotide on the target (i.e., $P_3$ is complementary to the 5'-end of the target). Therefore, the possible left extensions of the $P_3P_4P_5P_6$ core probe are probes S-3'-$AP_3P_4P_5$, S-3'-$TP_3P_4P_5$, S-3'-$CP_3P_4P_5$, and S-3'-$GP_3P_4P_5$. For the purposes of this illustration, T is assumed to be actually "correct," as A is in the complementary position in the target nucleic acid.

The upper left hand plot in FIG. 12D illustrates predicted hybridization data for the mismatch profile of the S-3'-$AP_3P_4P_5$ probe, with all data normalized to S-3'-$AP_3P_4P_5$. Data points for all substitutions at each of the 2–5 positions are shown, but the average data for the three substitutions at each position could also be utilized, a single substitution at each position can be utilized, the highest of the three values may be utilized, or some other combination. As shown in the S-3'-$AP_3P_4P_5$ graph, one point shows much higher binding affinity than the rest. This is the T substitution for A at position two. The renaming data in the $AP_3P_4P_5$ graph have the normal "smile" characteristics shown in FIG. 12B. Similar plots are developed for the C and G substitutions shown in the bottom portion of FIG. 12B. In each case, all datapoints are normalized to the presumed "core" probe in the graph.

The T extension graph, shown in the upper right hand portion of FIG. 12D, will not have aberrant curves like the 3'-$AP_3P_4P_5$ graph and others, because none of the monosubstitutions at position 2 of the 3'-$TP_3P_4P_5$ probe will be exactly complementary to the target. Accordingly, substitutions of A, C, and G at position 2 all produce the characteristic "smile" plots predicted for probes with single base mismatches relative to the target. In addition, the fluorescence intensity of the T substituted probe/target complex will normally be higher than the fluorescence intensity of the C, G, and A probe/target complexes. These data can be used in various combinations to determine which of the extensions is "correct" and thereby determine the sequence of the target nucleic acid.

From the data shown in FIGS. 12A to 12D, one concludes that the probe exactly complementary to the left extension of the target relative to the core probe complementary sequence has an A monomer at position 2 in the target.

This process is repeated until none of the graphs have appropriate characteristics, at which time it is concluded that an end of the target has been reached. Similarly, right extensions are evaluated until the end of the target (or end of the sequence of interest) is reached.

Figure 13:
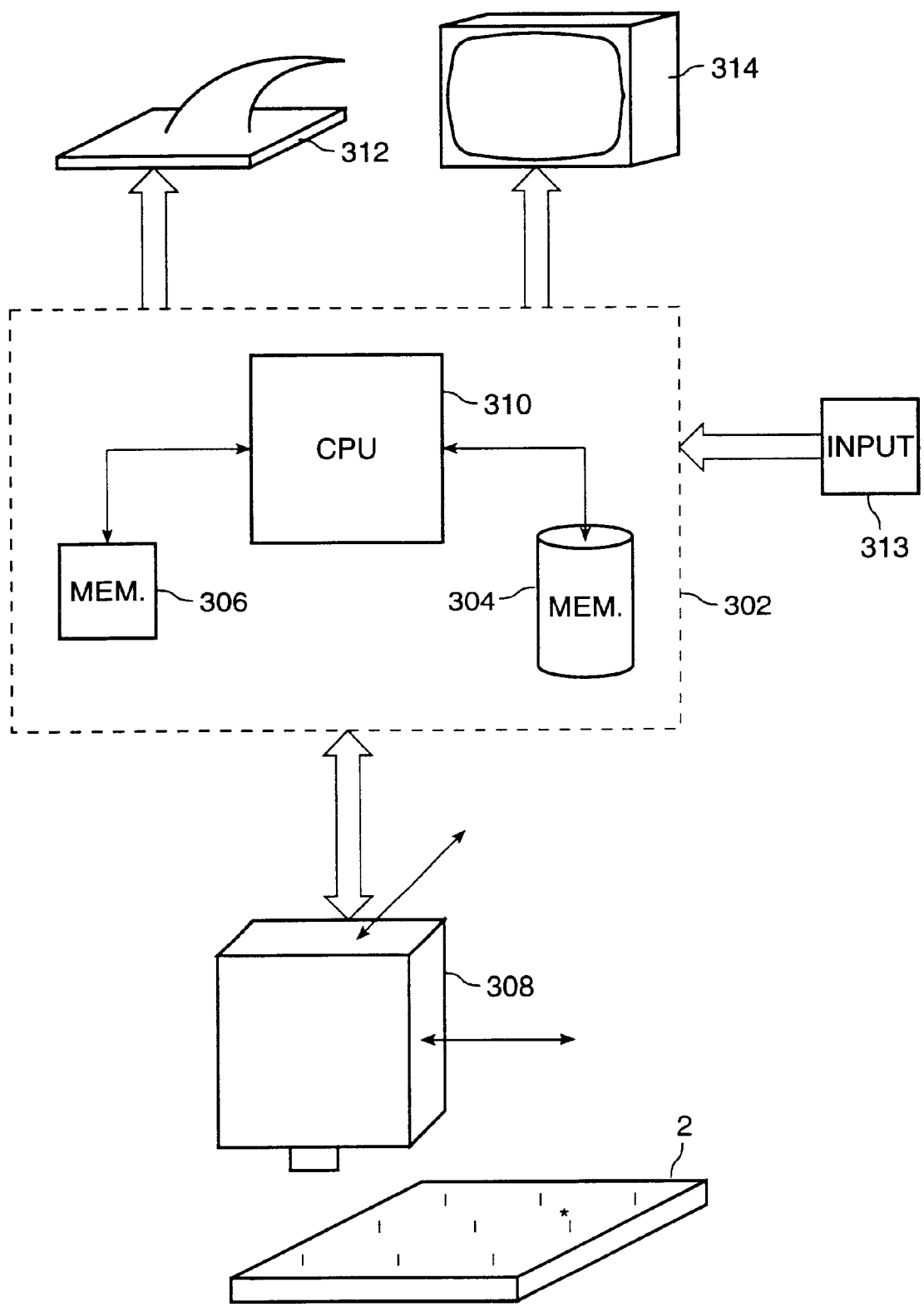
FIG. 13 illustrates a computer system for determining nucleotide sequence.

The above techniques can obviously be conducted through manual observation of the hybridization data. However, in preferred embodiments the data are analyzed using one or more appropriately programmed digital computers. An exemplary system is illustrated in FIG. 13. As shown therein, the system includes a computer or computers 302 operated under the control of a CPU and including memory 304, such as a hard disk, and memory 306, such as dynamic random access memory. The computer is used to control a scanning device 308 that measures the fluorescence intensity or other related information from a labeled target nucleotide coupled to portions of a substrate 2. The substrate 2 contains probe nucleotides of known sequence at known locations thereon. A user provides input via input devices 313.

Fluorescence intensity or other related information is stored in the memory 304/306. CPU 310 processes the fluorescence data to provide output to one or both of print device 312 or display 314. The data are processed according to the methods described herein, and output in the form of graphs such as those shown above, or in sequence of nucleic acid monomers, or in simple (+)/(−) output, or other results of the analysis of such data may be obtained. Suitable computers include, for example, an IBM PC or compatible, a SPARC workstation, or similar device.

Figure 14:
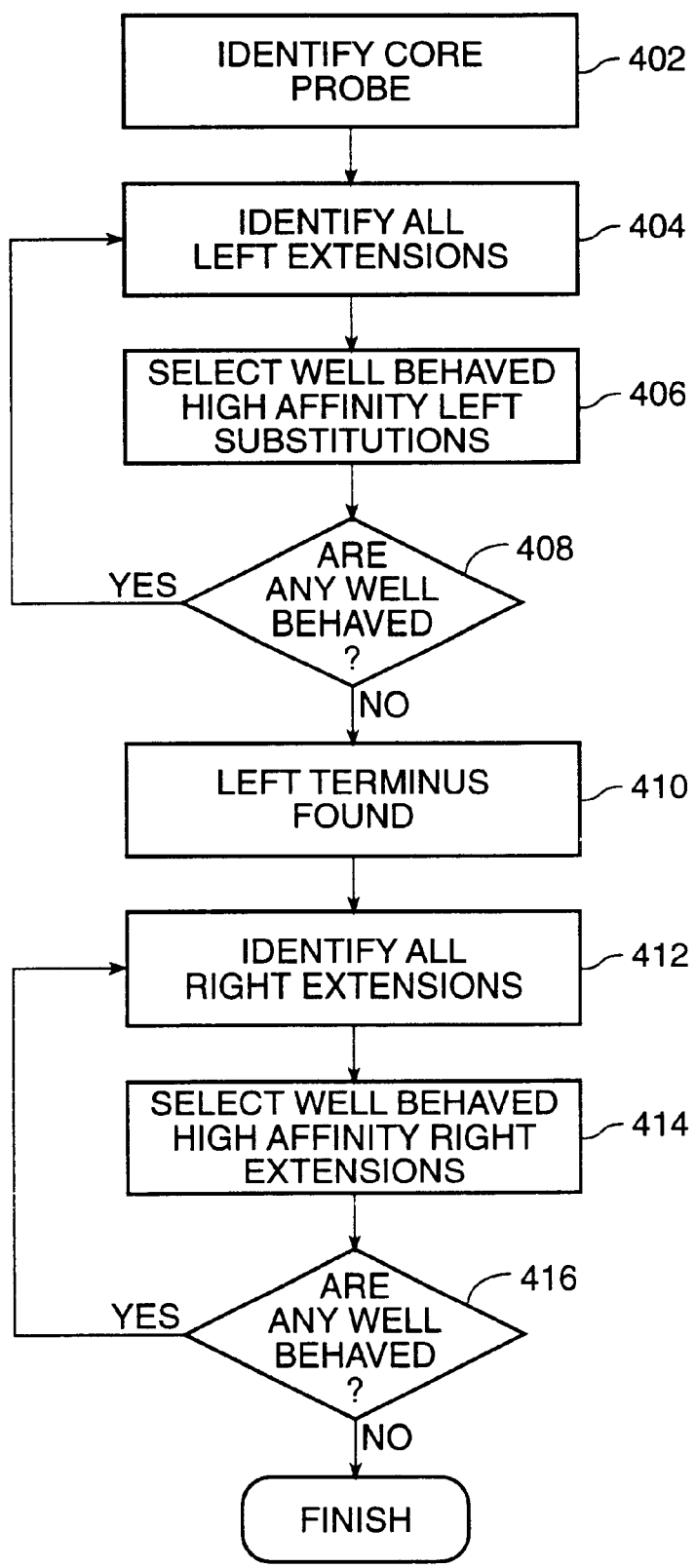
FIG. 14 illustrates a computer program for mismatch analysis and for determining the nucleotide sequence of a target nucleic acid.

FIG. 14 is a flowchart for a typical computer program used to evaluate an array of n-mers and identify the sequence of an exactly complementary (for mismatch analysis) or a larger k-mer (for sequencing or other purposes). As shown therein, the system first identifies a core probe at step 402 by, for example, selecting a probe having the highest binding affinity of some specified set of probes. The present method will often be operational in iterative processes, where the highest affinity probe in the array is not selected after the first iteration, and in other cases, it may be worthwhile, for example, to select the one, two, three, or more strongest binding probes and perform left and right extensions on each, then store and compare this information with other data before providing the final output. The results can aid confirmation of the correct sequence.

At step 404 the system identifies all left extensions of the core n-mer. At step 406 the system selects the appropriate left extension by one or both of:

determining which of the left extensions exhibits the behavior most consistent with a preset monomer substitution pattern, and/or selecting the left extension exhibiting the highest binding affinity.

The above selection criteria and others may in some embodiments be used in an AND fashion, i.e., both of the criteria must be met or the system assumes that one has either reached the terminal monomer or the system is not performing acceptably. In alternative embodiments, one of the criteria may be selected as a primary selection mechanism, and the other may be used to provide the user with warnings, potentially incorrect selections, or alternate selections.

Thereafter, the system determines if the selection criteria have met some minimum standard at step 408. If not, then the system assumes that the end of the sequence has been reached at step 410. If the selection criteria have been met, then the process is repeated beginning at step 404 with the new "core" selected as the correct extension from the previous core.

Thereafter, the process is effectively repeated for right extensions. At step 412 right extensions are identified. At step 414 a preset mismatch profile probe is identified and/or high affinity right extension. At step 416 the system determines if the terminus of the molecule has been reached. If not, then the process is repeated to step 412. If so, then the system assumes that the molecule has been sequenced, and the process is terminated with appropriate output to a printer or other output device.

D. Applications

The techniques described herein will have a wide range of applications, particularly wherever desired to determine if a target nucleic acid has a particular nucleotide sequence or some other sequence differing from a known sequence. For example, one application of the inventions herein is found in mutation detection. These techniques may be applied in a wide variety of fields including diagnostics, forensics, bioanalytics, and others.

For example, assume a "wild-type" nucleic acid has the sequence 5'-$N_1N_2N_3N_4$ where, again, N refers to a monomer such as a nucleotide in a nucleic acid and the subscript refers to position number. Assume that a target nucleic acid is to be evaluated to determine if it is the same as 5'-$N_1N_2N_3N_4$ or if it differs from this sequence, and so contains a mutation or mutant sequence. The target nucleic acid is initially exposed to an array of typically shorter probes, as discussed above. Thereafter, one or more "core" sequences are identified, each of which would be expected to have a high binding affinity to the target, if the target does not contain a mutant sequence or mutation. In this particular example, one probe that would be expected to exhibit high binding affinity would be the complement to 5'-$N_1N_2N_3$ (3'-$P_1P_2P_3$), assuming a 3-mer array is utilized. Again, it will be recognized that the probes and/or the target may be part of a longer nucleic acid molecule.

As an initial screening tool, the absolute binding affinity of the target to the 3'-$P_1P_2P_3$ probe will be utilized to determine if the first three positions of the target are of the expected sequence. If the complement to 5'-$N_1N_2N_3$ does not exhibit strong binding to the target, it can be properly concluded that the target is not of the wild-type.

The single base mismatch profile can also be utilized according to the present invention to determine if the target contains a mutant or wild-type sequence. FIGS. 15A and 15B illustrate typical illustrative plots resulting from targets that are wild-type (FIG. 15A) and mutant (FIG. 15B). As shown, the single base mismatch plots for wild-type targets generally follow the typical, smile-shaped plot. Conversely, when the target has a mutation at a particular position, not only will the absolute binding affinity of the target to a particular core probe be less, but the single base mismatch characteristics will deviate from expected behavior.

According to one aspect of the invention, a substrate having a selected group of nucleic acids (otherwise referred to herein as a "library" of nucleic acids") is used in the determination of whether a particular nucleic acid is the same or different than a wild-type or other expected nucleic acid. Libraries of nucleic acids will normally be provided as an array of probes or "probe array." Such probe arrays are preferably formed on a single substrate in which the identity of a probe is determined by ways of its location on the substrate. Optionally, such substrates will not only determine if the nucleotide sequence of a target is the same as the wild-type, but it will also provide sequence information regarding the target. Such substrates will find use in fields noted above such as in forensics, diagnostics, and others. Merely by way of specific example, the invention may be utilized in diagnostics associated with sickle cell anemia detection, detection of any of the large number of P-53 mutations, for any of the large number of cystic fibrosis mutations, for any particular variant sequence associated with the highly polymorphic HLA class 1 or class 2 genes (particularly class 2 DP, DQ and DR beta genes), as well as many other sequences associated with genetic diseases, genetic predisposition, and genetic evaluation.

When a substrate is to be used in such applications, it is not necessary to provide all of the possible nucleic acids of a particular length on the substrate. Instead, it will be necessary using the present invention to provide only a relatively small subset of all the possible sequences. For example suppose a target nucleic acid comprises a 5-base sequence of particular interest and that one wishes to develop a substrate that may be used to detect a single substitution in the 5-base sequence. According to one aspect of the invention, the substrate will be formed with the expected 5-base sequence formed on a surface thereof, along with all or most of the single base mismatch probes of the 5-base sequence. Accordingly, it will not be necessary to include all possible 5-base sequences on the substrate, although larger arrays will often be preferred. Typically, the length of the nucleic acid probes on the substrate according to the present invention will be between about 5 and 100 bases, between about 5 and 50 bases, between about 8 and 30 bases, or between about 8 and 15 bases.

By selection of the single base mismatch probes among all possible probes of a certain length, the number of probes on the substrate can be greatly limited. For example, in a 3-base sequence there are 69 possible DNA base sequences, but there will be only one exact complement to an expected sequence and 9 possible single base mismatch probes. By selecting only these probes, the diversity necessary for screening will be reduced. Preferably, but not necessarily, all of such single base mismatch probes are synthesized on a single substrate. While substrates will often be formed including other probes of interest in addition to the single base mismatches, such substrates will normally still have less than 50% of all the possible probes of n-bases, often less than 30% of all the possible probes of n-bases, often less than 20% of all the possible probes of n-bases, often less than 10% of the possible probes of n-bases, and often less than 5% of the possible probes of n-bases.

Nucleic acid probes will often be provided in a kit for analysis of a specific genetic sequence. According to one embodiment the kits will include a probe complementary to a target nucleic acid of interest. In addition, the kit will include single base mismatches of the target. The kit will normally include one or more of C, G, T, A and/or U single base mismatches of such probe. Such kits will often be provided with appropriate instructions for use of the complementary probe and single base mismatches in determining the sequence of a particular nucleic acid sample in accordance with the teachings herein. According to one aspect of the invention, the kit provides for the complement to the target, along with only the single base mismatches. Such kits will often be utilized in assessing a particular sample of genetic material to determine if it indicates a particular genetic characteristic. For example, such kits may be utilized in the evaluation of a sample as mentioned above in the detection of sickle cell anemia, detection of any of the large number of P-53 mutations, detection of the large number of cystic fibrosis mutations, detection of particular variant sequence associated with the highly polymorphic HLA class 1 or class 2 genes (particularly class 2 DP, DQ and DR beta genes), as well as detection of many other sequences associated with genetic diseases, genetic predisposition, and genetic evaluation.

Accordingly, it is seen that substrates with probes selected according to the present invention will be capable of performing many mutation detection and other functions, but will need only a limited number of probes to perform such functions.

EXAMPLES

1. $(G+T)^8$ Array and Differential Sequencing

Figure 16:
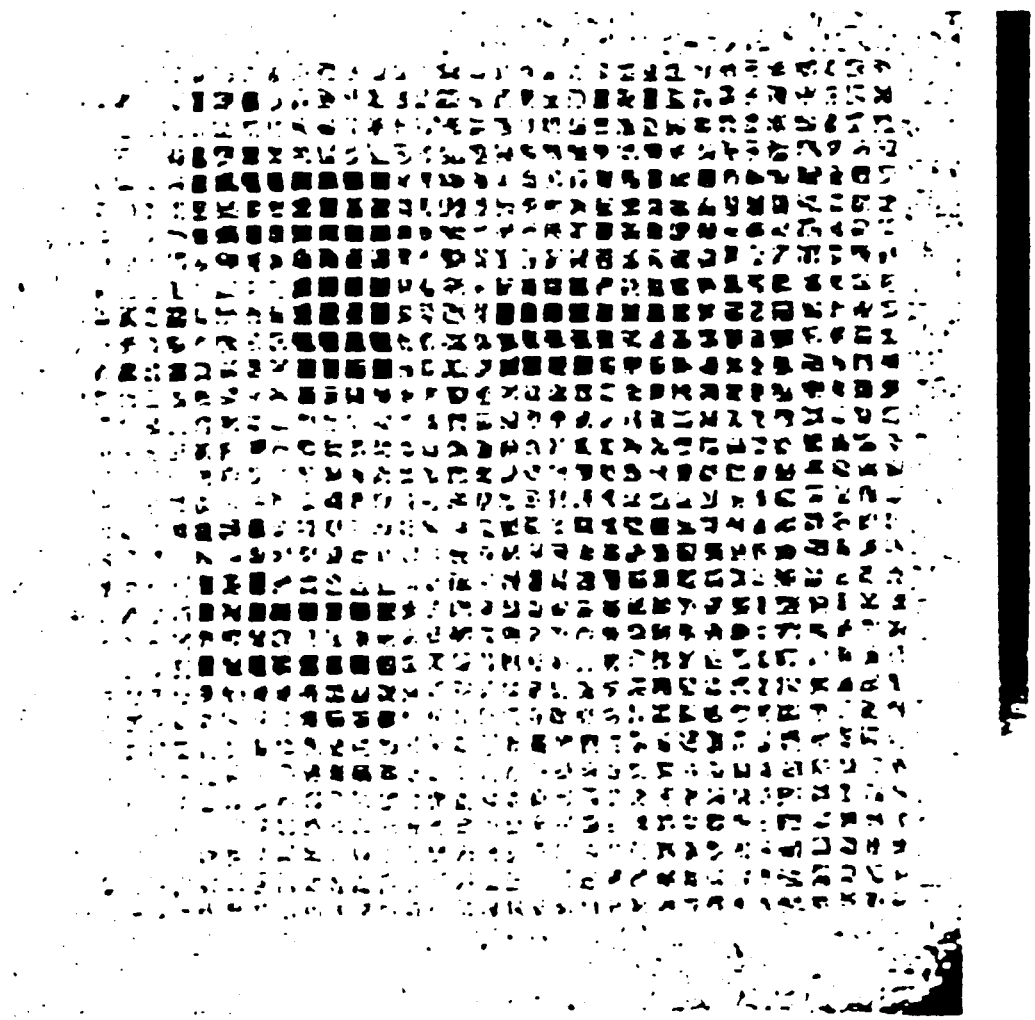
FIG. 16 is a fluorescence image of a single base mismatch test.
Figure 17A:
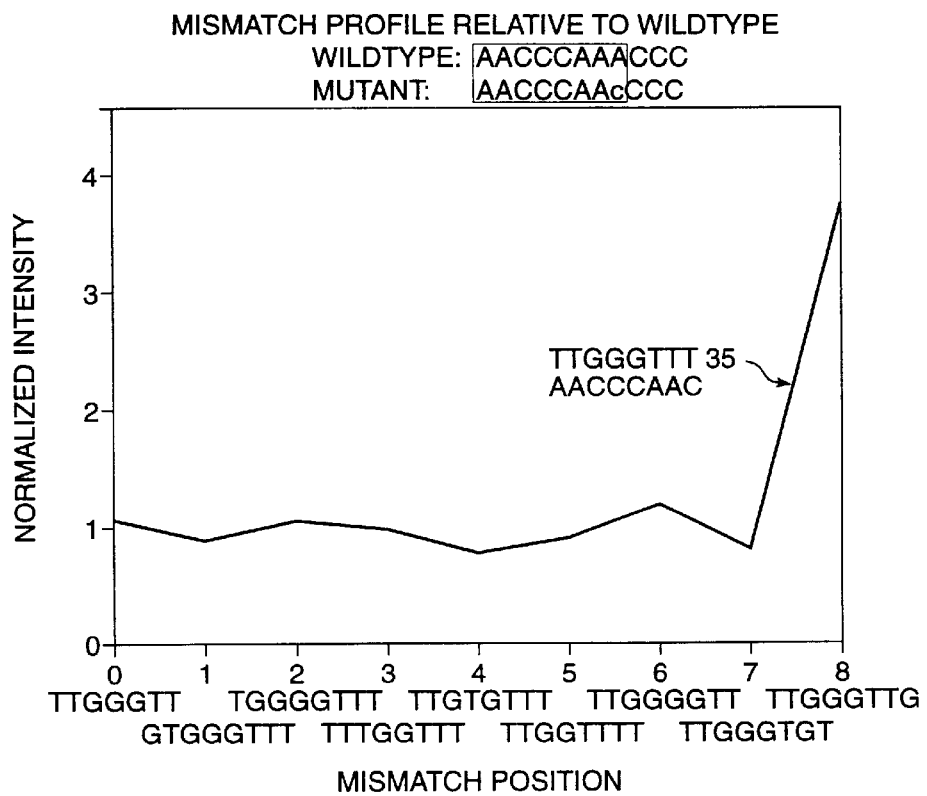
FIGS. 17A to 17D illustrate a technique for nucleic acid sequence identification. The SEQ. ID NOS. corresponding to the peptide sequences listed in the second and third lines of the headings for FIGS. 17a and 17b are 4 and 3, respectively. SEQ. ID NO:3 is identified in line 2 of the headings for FIGS. 17c and 17d.
Figure 17B:
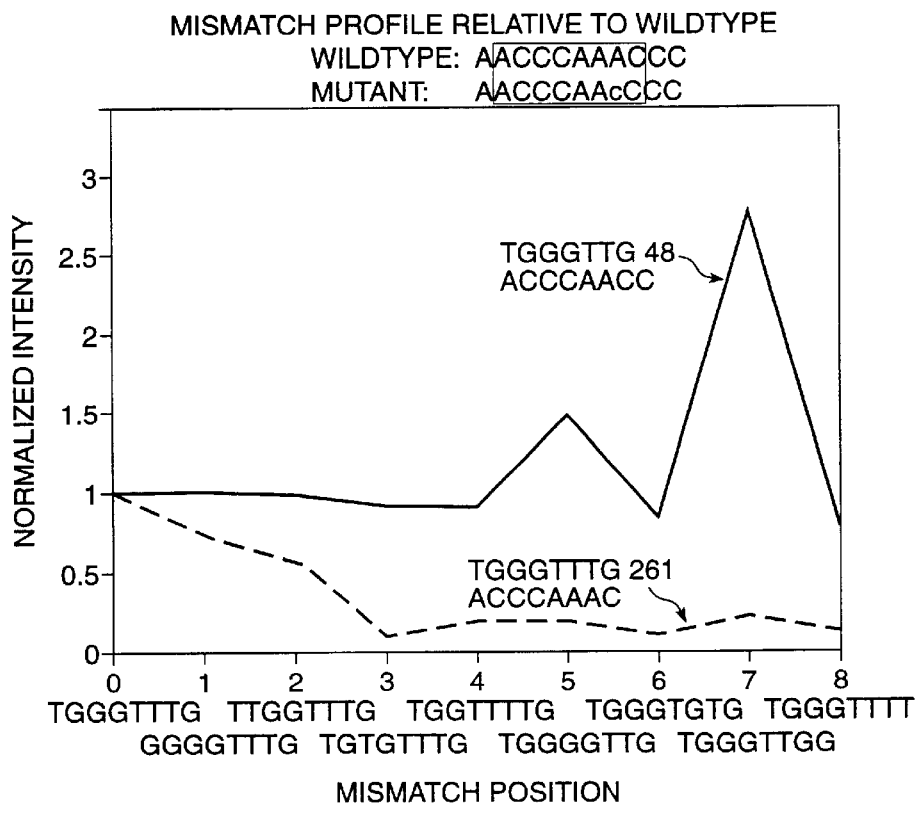

A $(G+T)^8$ array was prepared and incubated with 1 nM 5'-AACCCAA<u>C</u>CCC-fluorescein (SEQ. ID NO:3) (representing a mutant sequence when compared to 5'-AACCCAAACCC (SEQ. ID NO:4)), and scanned to test whether the sequence was "wild" or "mutant." The resulting image is given in FIG. 16. Four overlapping, exactly complementary octanucleotide probe/target hybridizations are expected if one is assuming the target should be 5'-AACCCAAACCC with probes: S-3'-TTGGGTTG, TGGGTTGG, GGGTTGGG, and GGTTGGGG. The results demonstrated that the effect of a single base change is quite dramatic, especially in the number and identity of the different mismatched probe/target complexes that form on the array. If one assumes the target nucleic acid generating the signal in FIG. 16 is 5'-AACCCAAACCC, (i.e., the wild-type) then the mismatch profiles for the complementary probe S-3'-TTGGGTTT are shown in FIG. 17A. The mismatch profile does not have the expected shape, and the probe/target complex has a low fluorescence intensity. The strong peak corresponding to a mismatch in position 8 indicates that the "correct" base in this position in the target is probably an A, because only A and C are found in the target in this experiment. Mismatch position 6 also shows a small peak. By contrast, a similar plot using the probe sequence S-3'-TTGGGTTG probe sequence as a core yielded the "smile" shape and high fluorescence intensity. In FIG. 17B the same profile for the next 8-mer probe is shown. The peaks have shifted one position to the left, again confirming that the sequence varies from wild-type at position 8 in the target. These correspond to the same positions in the original 11-mer target fragment. These data predict that there is a single base change in position 8 of the target, as compared to the wild-type.

Figure 17C:
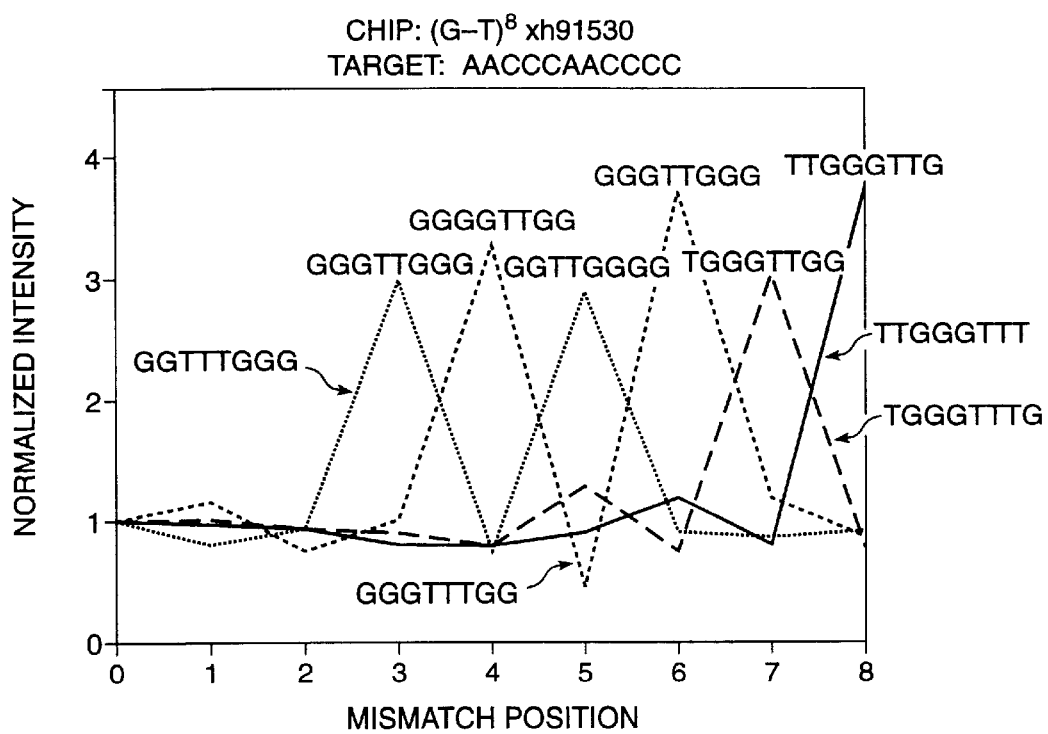
Figure 17D:
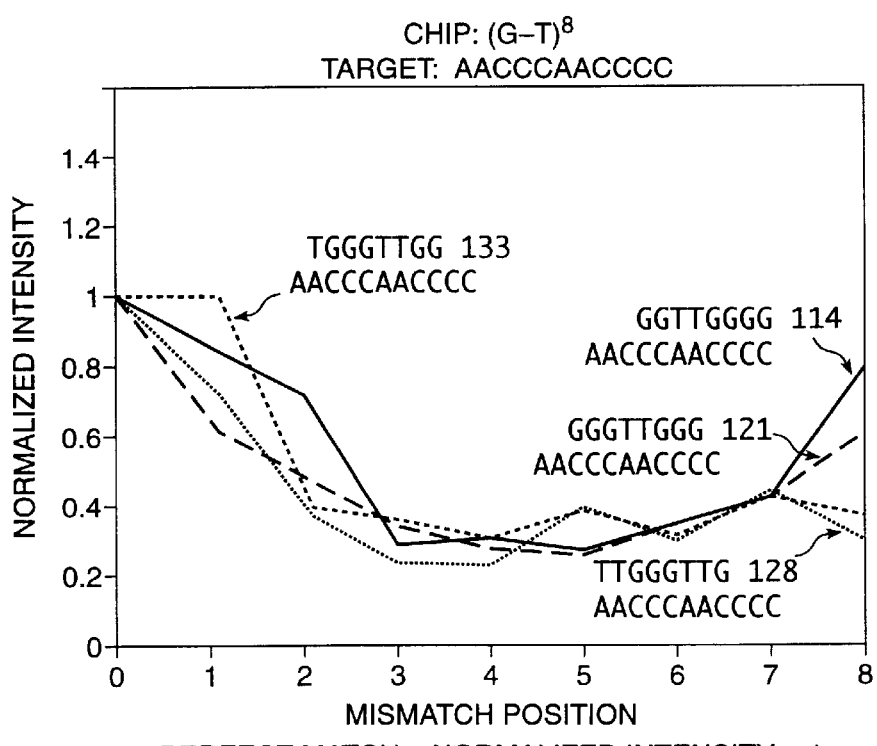

All of the mismatch probe profiles corresponding to the assumed fragment 5'-AACCCAACCCC, are shown in FIG. 17C. One observes the mutant position "moving" down the sequence. Finally, in FIG. 17D the mismatch plots are shown corresponding to the four probes that complement 5'-AACCCAACCCC, with the expected smile characteristics.

E. Conclusion

The present inventions provide improved methods and devices for the study of nucleotide sequences and nucleic acid interactions with other molecules. The above description is illustrative and not restrictive. Many variations of the invention will become apparent to those of skill in the art upon review of this disclosure. Merely by way of example certain of the inventions described herein will have application to other polymers such as peptides and proteins, and can utilize other synthesis techniques. The scope of the invention should, therefore, be determined not with reference to the above description, but instead should be determined with reference to the appended claims along with their full scope of equivalents.

What is claimed is:

1. A library of nucleic acid probes, said library consisting essentially of at least about 4 core probes which form an exact complement to a sequence in a target nucleic acid and n-base mismatches of said core probes, wherein n is between about 1 and 3, wherein said at least about 4 core probes and n-base mismatches of said core probes are covalently bound to a single substrate.

2. A library as recited in claim 1 wherein said nucleic acid probes are of a length between about 8 and 15 bases.

3. A library as recited in claim 1 wherein said library is on a single substrate.

4. A library as recited in claim 1 wherein said library comprises probes of n-bases or less, wherein n is equal to the number of bases in said target nucleic acid, and wherein said library comprises less than 50% of all possible probes of n-bases.

5. A library as recited in claim 1 wherein said library comprises probes of n-bases or less, wherein n is equal to the number of bases in said target nucleic acid, and wherein said library comprises less than 10% of all possible probes of n-bases.

6. A method of sequencing eleven consecutive bases in a target nucleic acid segment with a plurality of nucleic acid probes, comprising the steps of:

contacting said probes with said target;

identifying a first probe that hybridizes to said target;

selecting a first set of extension probes that comprise at least two of A, C, T, U, and G extensions of said first probe, wherein said first set of extension probes extends towards one end of said target nucleic acid; and identifying one of said first set of extension probes that hybridizes to said target more strongly than others of said first set of extension probes, whereby said one of said extension probes identifies a sequence in said target nucleic acid;

identifying single base mismatch probes, said single base mismatch probes comprising at least two of A, C, T, U, and G monosubstitutions of said first set of extension probes;

recording hybridization affinity data of said single base mismatch probes; and selecting one of said first set of extension probes wherein said hybridization affinity data of said single base mismatch probes conform to expected hybridization affinity data of said single base mismatch probes, wherein said expected hybridization data comprise probe/target complexes with a mismatch at termini of said extension probes exhibiting higher binding affinity than for substantially all of probe/target complexes with a mismatch at internal portions of said complexes, whereby said one of said first set of extension probes identifies a correct extension of said first probe.

7. A method as recited in claim 6 wherein substantially all of said nucleic acid probes comprise a same number of oligonucleotides, and wherein said extension probes comprise a sequence that is identical to a sequence of said first probe less one terminal nucleotide.

8. A method as recited in claim 6 further comprising the steps of:

selecting a second set of extension probes that comprise at least two of A, C, T, U, and G extensions of said first probe, wherein said second set of extension probes extends towards the opposite end of said first probe from said first set of extension probes; and identifying one of said second set of extension probes that hybridizes specifically to said target more strongly than others of said second set of extension probes, whereby said one of said second set of extension probes identifies a second base in said target nucleic acid.

9. The method as recited in claim 6 further comprising the step of:

repeating said steps of selecting sets of extension probes and identifying extension probes between about five and n times, wherein n is equal to the number of bases in said target nucleic acid.

10. The method as recited in claim 6 wherein:

said hybridization data are normalized to a hybridization value for one of said extension probes; and said step of identifying comprises selecting one of said extension probes having terminal single base mismatch probes that do not have normalized hybridization values higher than a normalized value of said one of said extension probes.

11. The method as recited in claim 6 wherein the step of identifying comprises the step of selecting one of said set of extension probes that exhibits a higher binding affinity to said target than other extension probes.

12. The method as recited in claim 6 wherein said step of identifying is conducted in a computer.

13. A method of determining if a nucleotide sequence of a target nucleic acid is the same as a sequence of a first nucleic acid comprising:

contacting said target nucleic acid to a plurality of nucleic acid probes;

determining the affinity of said target to probes identical to, but for a single base mismatch, of said subsequence; and determining that said nucleotide sequence of said target is the same as said first nucleic acid if said affinity of said target to probes identical to but for a single base mismatch follows a pattern, wherein said pattern comprises probe/target complexes with a mismatch at termini of said complexes exhibiting higher binding affinity than for substantially all of said probe/target complexes with a mismatch at internal portions of said complexes.

14. The method as recited in claim 13 wherein said pattern comprises affinity of said single base mismatch probes normalized to affinity of a perfect complement of said subsequence.

15. The method as recited in claim 14 wherein said affinity of single base mismatch probes are plotted as affinity versus mismatch position, and normalized to said affinity of a perfect complement of said subsequence.

16. The method as recited in claim 13 further comprising the step of determining that said nucleotide sequence of said target is not the same as said first nucleic acid if said affinity of said target to probes complementary to single base mismatches does not follow said pattern.

* * * * *

UNITED STATES PATENT AND TRADEMARK OFFICE
CERTIFICATE OF CORRECTION

PATENT NO.    : 6,284,460 B1
DATED         : September 4, 2001
INVENTOR(S)   : Fodor et al.

It is certified that error appears in the above-identified patent and that said Letters Patent is hereby corrected as shown below:

<u>Title page,</u>
Item [54], title should read: -- PROBE ARRAY, LIBRARY, AND METHOD OF IDENTIFYING A BASE IN A NUCLEIC ACID --

Signed and Sealed this

Twenty-seventh Day of August, 2002

Attest:

Attesting Officer

JAMES E. ROGAN
*Director of the United States Patent and Trademark Office*